US009803187B2

(12) United States Patent
Sherman et al.

(10) Patent No.: US 9,803,187 B2
(45) Date of Patent: Oct. 31, 2017

(54) BAULAMYCINS, COMPOSITIONS AND METHODS OF USE THEREOF

(71) Applicants: THE REGENTS OF THE UNIVERSITY OF MICHIGAN, Ann Arbor, MI (US); Asociación Instituto Nacional de Biodiversidad, Heredia (CR)

(72) Inventors: David H. Sherman, Ann Arbor, MI (US); Ashootosh Tripathi, Ypsilanti, MI (US); Michael Marie Kaufman-Schofield, Ann Arbor, MI (US); Giselle Tamayo, Heredia (CR); Pam Schultz, Superior Township, MI (US)

(73) Assignees: THE REGENTS OF THE UNIVERSITY OF MICHIGAN, Ann Arbor, MI (US); ASOCIACION INSTITUTO NACIONAL DE BIODIVERSIDAD, Heredia (CR)

( * ) Notice: Subject to any disclaimer, the term of this patent is extended or adjusted under 35 U.S.C. 154(b) by 43 days.

(21) Appl. No.: 14/717,096

(22) Filed: May 20, 2015

(65) Prior Publication Data

US 2015/0337288 A1 Nov. 26, 2015

Related U.S. Application Data

(60) Provisional application No. 62/000,783, filed on May 20, 2014.

(51) Int. Cl.
| | |
|---|---|
| *C12N 9/99* | (2006.01) |
| *C07C 49/248* | (2006.01) |
| *C07C 49/245* | (2006.01) |
| *C07C 49/217* | (2006.01) |
| *C07C 45/79* | (2006.01) |
| *C12N 9/00* | (2006.01) |
| *A61K 31/12* | (2006.01) |
| *C12N 1/20* | (2006.01) |

(52) U.S. Cl.
CPC ............... *C12N 9/99* (2013.01); *C07C 45/79* (2013.01); *C07C 49/217* (2013.01); *C07C 49/245* (2013.01); *C07C 49/248* (2013.01); *C12N 9/93* (2013.01); *A61K 31/12* (2013.01)

(58) Field of Classification Search
CPC ..... C07C 49/248; C07C 49/217; C07C 49/20; C07C 45/79; C07C 49/245; C07C 49/214; C12N 9/93; C12N 9/99
See application file for complete search history.

(56) References Cited

PUBLICATIONS

Tripathi, A, et al, "Baulamycins A and B, Broad-Spectrum Antibiotics Identified as Inhibitors of Siderophore Biosynthesis in Staphylococcus aureus and Bacillus anthracis" J. Am. Chem. Soc,. Jan. 2014, 136, 1579-1586. dx.doi.org/10.1021/ja4115924.*
Yirka, B. "Chemists deduce the correct structure of the A and B baulamycins" Phys.org, Jul. 27, 2017 (retrieved Aug. 30, 2017 from <URL:https://phys.org/news/2017-07-chemists-deduce-baulamycins.html>), 2 pages.*
Wu J; Lorenzo P; Zhong S; Ali M; Butts CP; Myers EL; Aggarwal VK "Synergy of synthesis, computation and NMR reveals correct baulamycin structures", Nature, Jul. 26, 2017, 547(7664), p. 436-440 . nature.com/articles/doi:10.1038/nature23265.*
"Antibiotic/Antimicrobial Resistance", Centers for Disease Control and Prevention, downloaded from the Internet at: <http://www.cdc.gov/drugresistance/index.html> (page last updated Aug. 2015).
Andersson et al., Persistence of antibiotic resistance in bacterial populations, FEMS Microbiol. Rev., 35(5):901-11 (2011).
Beasley et al., Mutation of L-2,3-diaminopropionic acid synthase genes blocks staphyloferrin B synthesis in Staphylococcus aureus, BMC Microbiol., 11:199 (2011).
Brandish et al., Modes of action of tunicamycin, liposidomycin B, and mureidomycin A: inhibition of phospho-N-acetylmuramyl-pentapeptide translocase from Escherichia coli, Antimicrob. Agents Chemother., 40(7):1640-4 (1996).
Cendrowski et al., Bacillus anthracis requires siderophore biosynthesis for growth in macrophages and mouse virulence, Mol. Microbiol., 51(2):407-17 (2004).
Challis, A widely distributed bacterial pathway for siderophore biosynthesis independent of nonribosomal peptide synthetases, Chembiochem., 6(4):601-11 (2005).
Cheung et al., Discovery of an iron-regulated citrate synthase in Staphylococcus aureus, Chem. Biol., 19(12):1568-78 (2012).
Cheung et al., Molecular characterization of staphyloferrin B biosynthesis in Staphylococcus aureus, Mol. Microbiol., 74(3):594-608 (2009).
Cruz et al., Titration-based screening for evaluation of natural product extracts: identification of an aspulvinone family of luciferase inhibitors, Chem. Biol., 18(11):1442-52 (2011).
Dale et al., Role of siderophore biosynthesis in virulence of Staphylococcus aureus: identification and characterization of genes involved in production of a siderophore, Infect. Immun., 71(1):29-37 (2004).
de Lorenzo et al., Aerobactin biosynthesis and transport genes of plasmid CoIV-K30 in Escherichia coli K-12, J. Bacteriol., 165(2):570-8 (1986).
de Lorenzo et al., Characterization of iucA and iucC genes of the aerobactin system of plasmid CoIV-K30 in Escherichia coli, J. Bacteriol., 167(1):350-5 (1986).
Drechsel et al., Purification and chemical characterization of staphyloferrin B, a hydrophilic siderophore from staphylococci, Biometals, 6(3):185-92 (1993).
Eschenfeldt et al., Cleavable C-terminal His-tag vectors for structure determination, J. Struct. Funct. Genomics, 11(1):31-9 (2010).
Ferraras et al., Small-molecule inhibition of siderophore biosynthesis in Mycobacterium tuberculosis and Yersinia pestis, Nat. Chem. Biol., 1(1):29-32 (2005).
Fischbach et al., Antibiotics for emerging pathogens, Science, 325(5944):1089-93 (2009).
Fox et al., The missing link in petrobactin biosynthesis: asbF encodes a (-)-3-dehydroshikimate dehydratase, Biochemistry, 47(47):12251-3 (2008).

(Continued)

*Primary Examiner* — Chris R Tate
*Assistant Examiner* — Aaron J Kosar
(74) *Attorney, Agent, or Firm* — Marshall, Gerstein & Borun LLP

(57) ABSTRACT

Provided herein are compositions of compounds of formula (I), methods of inhibiting a bacterial infection by contacting a cell with a composition comprising a compound of formula (I), and methods of isolating compounds of formula (I) from an extract of *Streptomyces tempisquensis*.

6 Claims, 7 Drawing Sheets

(56) References Cited

PUBLICATIONS

Gibson et al., The isolation and characterization of a hydroxamic acid (aerobactin) formed by Aerobacter aerogenes 62-I, Biochim. Biophys. Acta, 192(2):175-84 (1969).
Gupte et al., Inhibition of siderophore biosynthesis by 2-triazole substituted analogues of 5'-O-[N-(salicyl)sulfamoyl]adenosine: antibacterial nucleosides effective against *Mycobacterium tuberculosis*, J. Med. Chem., 51(23):7495-507 (2008).
Haag et al., Isolation and biological characterization of staphyloferrin B, a compound with siderophore activity from staphylococci, FEMS Microbiol. Lett., 115(2-3):125-30 (1994).
Haley et al., A battle for iron: host sequestration and *Staphylococcus aureus* acquisition, Microbes Infect., 14(3):217-27 (2012).
Hotta et al., Siderophore-mediated iron acquisition in Bacillus anthracis and related strains, Microbiology, 156(Pt. 7):1918-25 (2010).
Huang et al., Neaumycin: a new macrolide from *Streptomyces* sp. NEAU-x211, Org. Lett., 14(5):1254-7 (2012).
Itaya et al., A new micromethod for the colorimetric determination of inorganic phosphate, Clin. Chim. Acta, 14(3):361-6 (1966).
Kadi et al., Chapter 17. Siderophore biosynthesis a substrate specificity assay for nonribosomal peptide synthetase-independent siderophore synthetases involving trapping of acyl-adenylate intermediates with hydroxylamine, Methods Enzymol., 458:431-57 (2009).
Klevens et al., Invasive methicillin-resistant *Staphylococcus aureus* infections in the United States, JAMA, 298(15):1763-71 (2007).
Kong et al., Inhibition of MAO A and B by some plant-derived alkaloids, phenols and anthraquinones, J. Ethnopharmacol., 91(2-3):351-5 (2004).
Koppisch et al., Petrobactin is the primary siderophore synthesized by *Bacillus anthracis* str. Sterne under conditions of iron starvation, Biometals, 18(6):577-85 (2005).
Lee et al., Biosynthetic analysis of the petrobactin siderophore pathway from Bacillus anthracis, J. Bacteriol., 189(5):1698-710 (2007).
Livermore et al., Discovery research: the scientific challenge of finding new antibiotics, J. Antimicrob. Chemother., 66(9):1941-4 (2011).
Magarvey et al., Isolation and characterization of novel marine-derived actinomycete taxa rich in bioactive metabolites, Appl. Environ. Microbiol., 70(12):7520-9 (2004).
Matsumori et al., Stereochemical Determination of Acyclic Structures Based on Carbon-Proton Spin-Coupling Constants. A Method of Configuration Analysis for Natural Products, J. Org. Chem., 64(3):866-76 (1999).
McQuade et al., A nonradioactive high-throughput assay for screening and characterization of adenylation domains for nonribosomal peptide combinatorial biosynthesis, Anal. Biochem., 386(2):244-50 (2009).
Miethke et al., Siderophore-based iron acquisition and pathogen control, Microbiol. Mol. Biol. Rev., 71(3):413-51 (2007).
Moir et al., New classes of antibiotics, Curr. Opin. Pharmacol., 12(5):535-44 (2012).
Montaser et al., Marine natural products: a new wave of drugs?, Future Med. Chem., 3(12):1475-89 (2011).
Morinaka et al., Mollenyne A, a long-chain chlorodibromohydrin amide from the sponge Spirastrella mollis, Org. Lett., 13(24):6338-41 (2011).
Nathan, Fresh approaches to anti-infective therapies, Sci. Transl. Med., 4(140):140rs2 (2012).
Neres et al., Inhibition of siderophore biosynthesis in *Mycobacterium tuberculosis* with nucleoside bisubstrate analogues: structure-activity relationships of the nucleobase domain of 5'-O-[N-(salicyl)sulfamoyl]adenosine, J. Med. Chem., 51(17):5349-70 (2008).
Newman et al., Natural products as sources of new drugs over the 30 years from 1981 to 2010, J. Nat. Prod., 75(3):311-35 (2012).
Newman et al., Natural products as sources of new drugs over the last 25 years, J. Nat. Prod., 70(3):461-77 (2007).
Nusca et al., Functional and structural analysis of the siderophore synthetase AsbB through reconstitution of the petrobactin biosynthetic pathway from Bacillus anthracis, J. Biol. Chem., 287(19):16058-72 (2012).
Oves-Costales et al., Enzymatic logic of anthrax stealth siderophore biosynthesis: AsbA catalyzes ATP-dependent condensation of citric acid and spermidine, J. Am. Chem. Soc., 129(27):8416-7 (2007).
Oves-Costales et al., The long-overlooked enzymology of a nonribosomal peptide synthetase-independent pathway for virulence-conferring siderophore biosynthesis, Chem. Commun. (Camb.), 43:6530-41 (2009).
Pegan et al., A universal, fully automated high throughput screening assay for pyrophosphate and phosphate release from enzymatic reactions, Comb. Chem. High Throughput Screen, 13(1):27-38 (2010).
Peng et al., Structure and absolute configuration of karlotoxin-2, an ichthyotoxin from the marine dinoflagellate Karlodinium veneficum, J. Am. Chem. Soc., 132(10):3277-9 (2010).
Pfleger et al., Characterization and analysis of early enzymes for petrobactin biosynthesis in Bacillus anthracis, Biochemistry, 46(13):4147-57 (2007).
Pfleger et al., Structural and functional analysis of AsbF: origin of the stealth 3,4-dihydroxybenzoic acid subunit for petrobactin biosynthesis, Proc. Natl. Acad. Sci. USA, 105(44):17133-8 (2008).
Quadri, Strategic paradigm shifts in the antimicrobial drug discovery process of the 21st century, Infect. Disord. Drug Targets, 7(3):230-7 (2007).
Rainey et al., The genus *Nocardiopsis* represents a phylogenetically coherent taxon and a distinct actinomycete lineage: proposal of Nocardiopsaceae fam. nov, Int. J. Syst. Bacteriol., 46(4):108892 (1996).
Roemer et al., Confronting the challenges of natural product-based antifungal discovery, Chem. Biol., 18(2):148-64 (2011).
Schmelz et al., Structural basis for acyl acceptor specificity in the achromobactin biosynthetic enzyme AcsD, J. Mol. Biol., 412(3):495-504 (2011).
Somu et al., Rationally designed nucleoside antibiotics that inhibit siderophore biosynthesis of *Mycobacterium tuberculosis*, J. Med. Chem., 49(1):31-4 (2006).
Stols et al., A new vector for high-throughput, ligation-independent cloning encoding a tobacco etch virus protease cleavage site, Protein Expr. Purif., 25(1):8-15 (2002).
Sweeney et al., Anthrax infection, Am. J. Respir. Crit. Care Med., 184(12):1333-41 (2011).
Upson et al., A spectrophotometric method to measure enzymatic activity in reactions that generate inorganic pyrophosphate, Anal. Biochem., 243(1):41-5 (1996).
Warner et al., ColV plasmid-specific aerobactin synthesis by invasive strains of *Escherichia coli*, Infect. Immun., 33(2):540-5 (1981).
Webb, A continuous spectrophotometric assay for inorganic phoSphate and for measuring phosphate release kinetics in biological systems, Proc. Natl. Acad. Sci. USA, 89(11):4884-7 (1992).
Wilson et al., A continuous kinetic assay for adenylation enzyme activity and inhibition, Anal. Biochem., 404(1):56-63 (2010).
Zhang et al., A Simple Statistical Parameter for Use in Evaluation and Validation of High Throughput Screening Assays, J. Biomol. Screen, 4(2):67-73 (1999).

\* cited by examiner

BAULAMYCINS, COMPOSITIONS AND METHODS OF USE THEREOF

CROSS REFERENCE TO RELATED APPLICATIONS

This application claims benefit under 35 U.S.C. §119 to U.S. Provisional Application No. 62/000,783, filed May 20, 2014, the disclosure of which is incorporated by reference in its entirety herein.

STATEMENT OF GOVERNMENT INTERESTS

This invention was made with government support under TW007404 awarded by the National Institutes of Health and support under DGE1256260 awarded by the National Science Foundation. The Government has certain rights in the invention.

INCORPORATION BY REFERENCE OF MATERIAL SUBMITTED ELECTRONICALLY

Incorporated by reference in its entirety is a computer-readable nucleotide/amino acid sequence listing submitted concurrently herewith and identified as follows: ASCII (text) file named "47514A_SeqListing.txt,"-573 bytes, created Aug. 3, 2015.

BACKGROUND

The rapid ability of pathogens to develop resistance to antibiotics is endangering the management of a multitude of serious infections.[1-3] In alarming contrast to the increase of bacterial adaptation to currently marketed drugs, the discovery of novel classes of antimicrobials is on the decline.[4] Although the majority of pharmaceutical efforts during the past six decades have focused on the synthetic enhancement of a limited set of unique core scaffolds, a more sustainable route to combat antibiotic resistance is the discovery of novel chemical structures possessing unique microbial targets.[2,5] Iron acquisition mechanisms in particular may represent effective antimicrobial targets that present substantial hurdles to bacterial antibiotic resistance.[6] Iron is required for growth and survival of bacteria but remains tightly regulated in the mammalian host. Many pathogenic Gram-positive and Gram-negative bacteria utilize virulence-associated siderophores to scavenge iron from this restricted environment and return it to the microbial cell.[7] Although previous studies have corroborated siderophore biosynthetic enzymes as effective drug targets through the tailoring of established chemical scaffolds,[8-11] no novel chemical structures have been identified.

In our efforts to identify new structural antibiotic classes with inhibitory activity against siderophore biosynthetic enzymes, the Gram-positive bacteria methicillin-resistant Staphylococcus aureus (MRSA) and Bacillus anthracis were selected as model systems. The "superbug" MRSA is a major public health concern, attributed to more than 18,000 deaths a year in the United States.[2-12] In contrast, the spore-forming microorganism B. anthracis is the causative agent of anthrax. The ability of the bacterium to quickly achieve high concentrations within infected hosts makes it a serious bioterrorism threat, with mortality rates for inhalational infection historically reaching as high as 94%.[13]

Both pathogens are strongly associated with antimicrobial resistance,[14] and their siderophore biosynthetic pathways have been extensively characterized.[15,16] The siderophores staphyloferrin B (2) of S. aureus[17-22] and petrobactin (5) of B. anthracis[23-30] in particular have been shown to be critical for survival in iron-limited environments.

The biosynthetic pathways for both siderophores involve a type A nonribosomal peptide synthetase independent siderophore (NIS) synthetase, SbnE (FIG. 1A) in staphyloferrin B and AsbA (FIG. 1B) in petrobactin. Type A NIS synthetases are a unique class of enzymes found within siderophore biosynthetic pathways of a number of pathogenic bacteria, including Shigella flexneri, Escherichia coli, and Salmonella typhimurium.[31,32] These enzymes catalyze the condensation of citric acid with either a polyamine or amino alcohol substrate in an ATP-dependent reaction.[31,32] Since type A NIS synthetases share similar catalytic mechanisms and substrate preferences, novel antibiotics against S. aureus or B. anthracis that could also serve as broad-spectrum antibiotics against other NIS synthetase-containing pathogens were investigated.

SUMMARY

Provided herein are compounds of formula (I) or salts thereof, and compositions further comprising a pharmaceutically acceptable excipient:

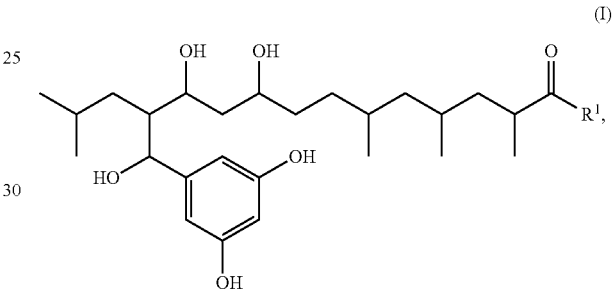

wherein $R^1$ is a $C_{1-6}$alkyl. In various cases, $R^1$ is methyl or ethyl. In some specific cases, R1 is ethyl. In some specific cases, $R^1$ is methyl. In some cases, the compound of formula (I) has a relative stereochemistry as shown in formula (IA):

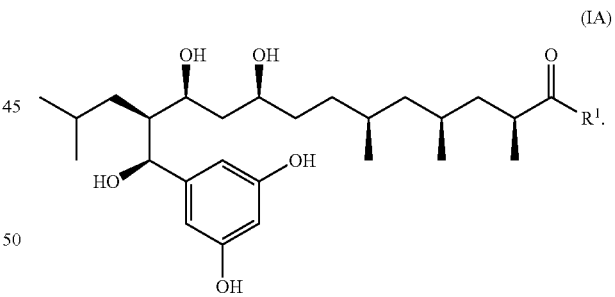

The compound can have a structure

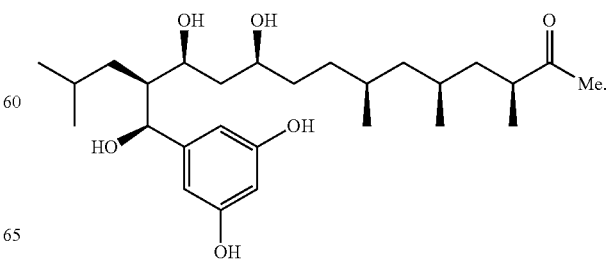

The compound can have a structure

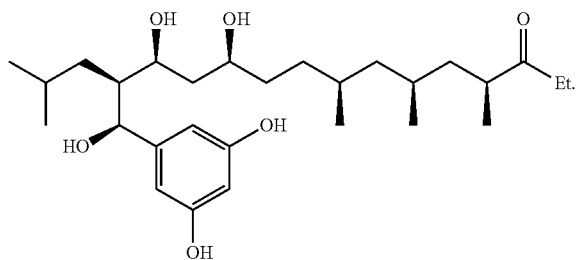 [SMILES: CCC(=O)[C@@H](C)C[C@@H](C)C[C@@H](C)CC[C@H](O)C[C@H](O)[C@H](CC(C)C)[C@H](O)c1cc(O)cc(O)c1]

Also provided herein are methods of inhibiting a nonribosomal peptide synthetase independent siderophore (NIS) synthetase comprising contacting the NIS synthetase with a composition as disclosed herein, in an amount sufficient to inhibit the NIS synthetase. In various cases, the NIS synthetase can be a Type A NIS synthetase. In various cases, the NIS synthetase is AsbA or SbnE.

Further provided are methods of treating a condition due to a bacterial infection in a cell comprising contacting the cell with a composition as disclosed herein. The contacting can be in vivo or in vitro. The bacterial infection can be due to Staphylococcus aureus, methicillin resistant S. aureus, Bacillus anthracis, Escherichia coli, Shigella flexneri, or Salmonella typhimurium. In some cases, the bacteria are MRSA. In various cases, the cell is a mammalian cell (e.g., a human cell). In some cases, the cell is an animal cell.

Further provided are methods of extracting a compound of formula (I) from an extract from Streptomyces tempisquensis comprising subjecting the extract to chromatography. In various cases, the chromatography comprises one or more of fractionation, high performance liquid chromatography, and reverse phase liquid chromatography. In some cases, the extract is subjected to C18 fractionation followed by reverse phase HPLC.

DETAILED DESCRIPTION

Figure 1:
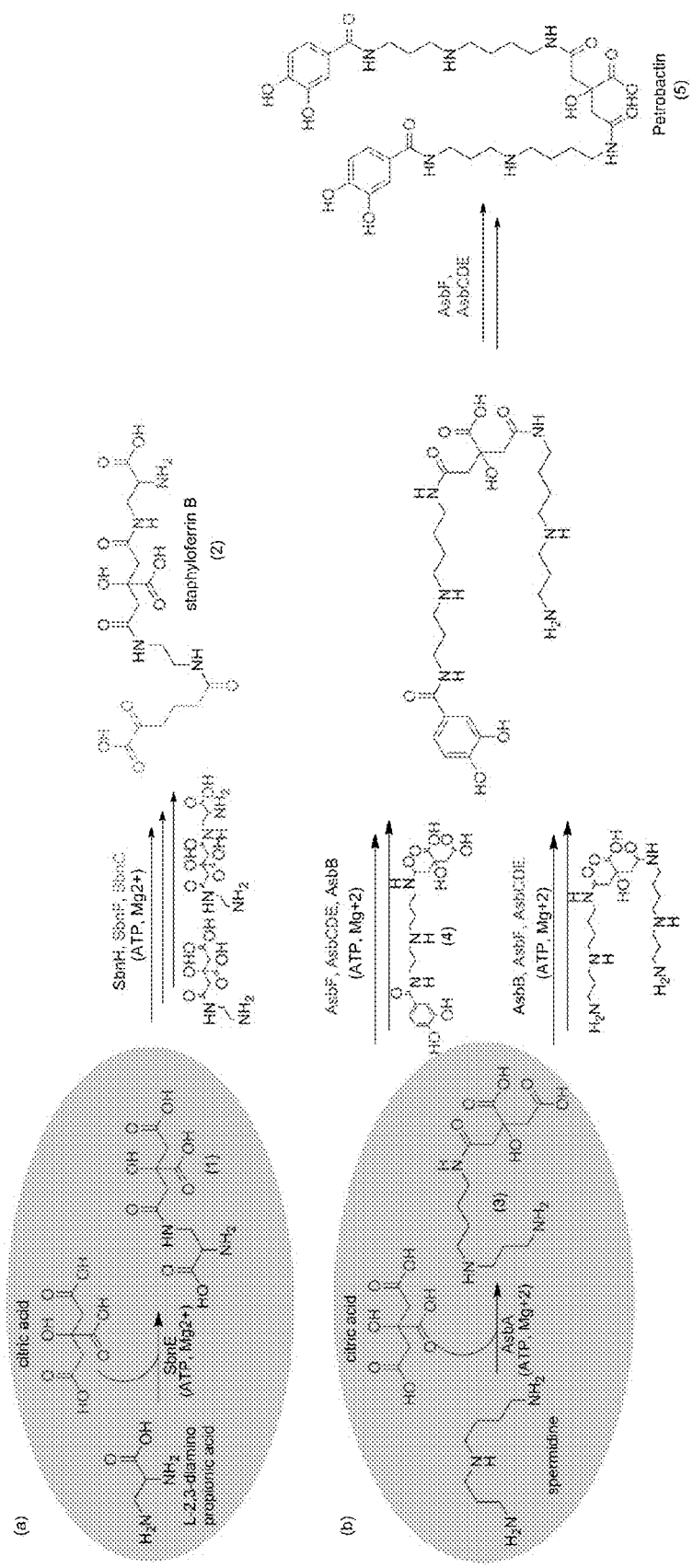
FIG. 1. Biosynthesis of the virulence-associated siderophore (A) staphyloferrin B in S. aureus (B) petrobactin in B. anthra-cis. The target biosynthetic enzymes, SbnE and AsbA, encircled.
Figure 2:
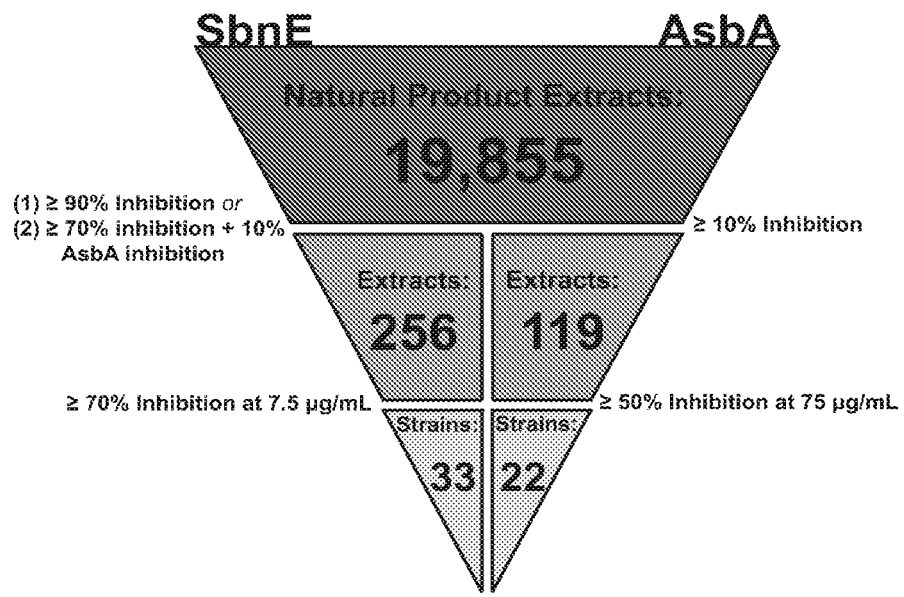
FIG. 2. Triage of hits derived during high throughput screening of SbnE and AsbA against the full microbial NPE library.

Provided herein are compositions comprising a compound of formula (I), or a pharmaceutically acceptable salt thereof:

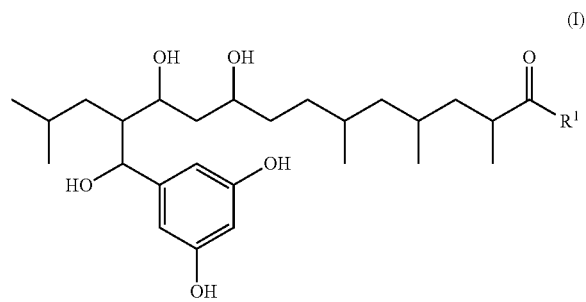

and a pharmaceutically acceptable excipient,
wherein $R^1$ is a $C_{1-6}$alkyl, for example, methyl or ethyl. In some cases, the compound of formula (I) has stereochemistry as shown in formula (IA):

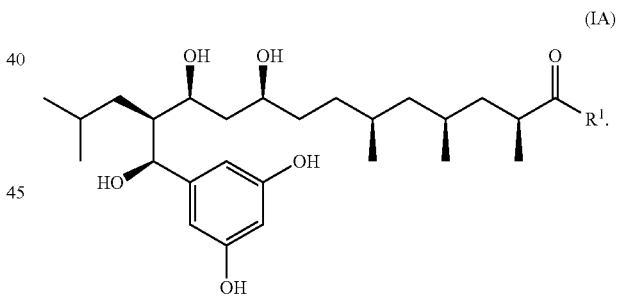

The compositions discloses herein are useful in inhibiting nonribosomal peptide synthetase independent siderophore (NIS) synthetase. Examples of such NIS synthetases include a Type A NIS synthetase and AsbA and SbnE. The inhibition of NIS synthetases can be useful as an antibiotic, e.g., against S. aureus, B. anthracis, E. coli, S. flexneri, and S. typhimurium.

Compounds of Formula (I)

Compounds as disclosed herein can be extracted from Streptomyces tempisquensis, as described in detail in the examples.

Pharmaceutical Formulations and Routes of Administration

Compositions of compounds as disclosed herein are provided. In some embodiments, compositions are provided that comprise an effective amount of a compound as disclosed herein and an acceptable excipient. In some cases, the excipient is a pharmaceutically acceptable carrier.

The term "effective amount" as used herein, refer to an amount of a compound sufficient to affect the desired outcome, e.g., to inhibit the intended target (e.g., one or more NIS synthetases), or to treat, ameliorate, or prevent the identified disease or condition (e.g., as an antibiotic against a bacterial infection), or to exhibit a detectable therapeutic, prophylactic, or inhibitory effect (e.g., against an infection of one or more of S. aureus, B. anthracis, E. coli, S. flexneri, and S. typhimurium). The effect can be detected by, for example, an improvement in clinical condition, reduction in symptoms, or by any of the assays or clinical diagnostic tests described herein. The precise effective amount for a subject will depend upon the subject's body weight, size, and health; the nature and extent of the condition; and the therapeutic or combination of therapeutics selected for administration. Therapeutically and prophylactically effective amounts for a given situation can be determined by routine experimentation that is within the skill and judgment of the clinician.

Compositions can comprise an amount of a compound as disclosed herein of 0.01 mg to 5 g. Specific ranges of amounts of a compound as disclosed herein include 0.1 mg to 1000 mg, 1 mg to 500 mg, 1 mg to 400 mg, 1 mg to 300 mg, 1 mg to 200 mg, 1 mg to 150 mg, and 1 mg to 100 mg. Additionally or alternatively, the amount of compound in a composition as disclosed herein is measured in mg/kg. Contemplated mg/kg doses of the disclosed compounds include about 0.001 mg/kg to about 1000 mg/kg. Specific ranges of doses in mg/kg include about 0.1 mg/kg to about 500 mg/kg, about 0.5 mg/kg to about 200 mg/kg, about 1 mg/kg to about 100 mg/kg, about 2 mg/kg to about 50 mg/kg, and about 5 mg/kg to about 30 mg/kg.

In various embodiments, administration of a composition as disclosed herein is by a single administration of the composition, or can be administered over a period of time, either in divided doses or in a continuous-release composition or administration method (e.g., a pump). However the compounds of the embodiments are administered to the subject, the amounts of compound administered and the route of administration chosen should be selected to permit efficacious treatment of the disease condition. The composition can be administered once per day, twice per day, three times per day, four times per day, once every other day, once every third day, once a week, once a month, once every other month, once every six months, or once a year.

The term "pharmaceutically acceptable excipient" refers to an excipient for administration of a pharmaceutical agent, such as the compounds described herein. The term refers to any pharmaceutical excipient that may be administered without undue toxicity. Excipients include carriers, solvents, stabilizers, adjuvants, diluents, etc.

Pharmaceutically acceptable excipients are determined in part by the particular composition being administered, as well as by the particular method used to administer the composition. Accordingly, there exists a wide variety of suitable formulations of pharmaceutical compositions (see, e.g., Remington's Pharmaceutical Sciences).

Suitable excipients may be carrier molecules that include large, slowly metabolized macromolecules such as proteins, polysaccharides, polylactic acids, polyglycolic acids, polymeric amino acids, amino acid copolymers, and inactive virus particles. Other exemplary excipients include antioxidants (e.g., ascorbic acid), chelating agents (e.g., EDTA), carbohydrates (e.g., dextrin, hydroxyalkylcellulose, and/or hydroxyalkylmethylcellulose), stearic acid, liquids (e.g., oils, water, saline, glycerol and/or ethanol) wetting or emulsifying agents, pH buffering substances, and the like. Liposomes are also included within the definition of pharmaceutically acceptable excipients.

In some embodiments, the pharmaceutical composition is formulated to achieve a physiologically compatible pH, and may range from a pH of about 3 to a pH of about 11, about pH 3 to about pH 7, depending on the formulation and route of administration. In alternative embodiments, the pH is adjusted to a range from about pH 5.0 to about pH 8. More particularly, in various cases, the pharmaceutical compositions comprise a therapeutically or prophylactically effective amount of at least one compound as described herein, together with one or more pharmaceutically acceptable excipients.

The compound or composition comprising the compound is administered by any route that permits treatment of the disease or condition. One route of administration is oral administration. Additionally, the compound or composition comprising the compound may be delivered to a patient using any standard route of administration, including parenterally, such as intravenously, intraperitoneally, intrapulmonary, subcutaneously or intramuscularly, intrathecally, topically, transdermally, rectally, orally, nasally or by inhalation. Slow release compositions are be prepared from the agents described herein in order to achieve a controlled release of the active agent in contact with the body fluids in the gastro intestinal tract, and to provide a substantial constant and effective level of the active agent in the blood plasma. In some cases, the crystal form of a compound as disclosed herein is embedded for this purpose in a polymer matrix of a biological degradable polymer, a water-soluble polymer or a mixture of both, and optionally suitable surfactants. Embedding can mean in this context the incorporation of micro-particles in a matrix of polymers. Controlled release formulations are also obtained through encapsulation of dispersed micro-particles or emulsified micro-droplets via known dispersion or emulsion coating technologies.

The pharmaceutical compositions described herein are formulated in any form suitable for an intended method of administration. When intended for oral use for example, tablets, troches, lozenges, aqueous or oil suspensions, non-aqueous solutions, dispersible powders or granules (including micronized particles or nanoparticles), emulsions, hard or soft capsules, syrups or elixirs may be prepared. Compositions intended for oral use may be prepared according to any method known to the art for the manufacture of pharmaceutical compositions, and such compositions may contain one or more agents including sweetening agents, flavoring agents, coloring agents and preserving agents, in order to provide a palatable preparation.

Compositions, e.g., for parenteral or oral administration, are most typically solids, liquid solutions, emulsions or suspensions, while inhalable formulations for pulmonary administration are generally liquids or powders. In various cases, a pharmaceutical composition is formulated as a lyophilized solid that is reconstituted with a physiologically compatible solvent prior to administration. Alternative pharmaceutical compositions are formulated as syrups, creams, ointments, tablets, and the like.

Pharmaceutically acceptable excipients particularly suitable for use in conjunction with tablets include, for example, inert diluents, such as celluloses, calcium or sodium carbonate, lactose, calcium or sodium phosphate; disintegrating agents, such as cross-linked povidone, maize starch, or alginic acid; binding agents, such as povidone, starch, gelatin or acacia; and lubricating agents, such as magnesium stearate, stearic acid or talc.

Tablets may be uncoated or may be coated by known techniques including microencapsulation to delay disintegration and adsorption in the gastrointestinal tract and thereby provide a sustained action over a longer period. For example, a time delay carrier such as glyceryl monostearate or glyceryl distearate alone or with a wax may be employed.

Compositions for oral use may be also presented as hard gelatin capsules wherein the active ingredient is mixed with an inert solid excipient, for example celluloses, lactose, calcium phosphate or kaolin, or as soft gelatin capsules wherein the active ingredient is mixed with non-aqueous or oil medium, such as glycerin, propylene glycol, polyethylene glycol, peanut oil, liquid paraffin or olive oil.

In another embodiment, pharmaceutical compositions are formulated as suspensions comprising a compound of the embodiments in admixture with at least one pharmaceutically acceptable excipient suitable for the manufacture of a suspension.

In yet another embodiment, pharmaceutical compositions are formulated as dispersible powders and granules suitable for preparation of a suspension by the addition of suitable excipients.

Excipients suitable for use in connection with suspensions include suspending agents (e.g., sodium carboxymethylcellulose, methylcellulose, hydroxypropyl methylcellulose, sodium alginate, polyvinylpyrrolidone, gum tragacanth, gum acacia); dispersing or wetting agents (e.g., a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycethanol), a condensation product of ethylene oxide with a partial ester derived from a fatty acid and a hexitol anhydride (e.g., polyoxyethylene sorbitan monooleate)); and thickening agents (e.g., carbomer, beeswax, hard paraffin or cetyl alcohol). In some cases, the suspensions also contain one or more preservatives (e.g., acetic acid, methyl or n-propyl p-hydroxy-benzoate); one or more coloring agents; one or more flavoring agents; and one or more sweetening agents such as sucrose or saccharin.

In various embodiments, the pharmaceutical compositions are oil-in water emulsions. The oily phase may be a vegetable oil, such as olive oil or arachis oil, a mineral oil, such as liquid paraffin, or a mixture of these. Suitable excipients for oil-in-water emulsions include emulsifying agents such as naturally-occurring gums, such as gum acacia and gum tragacanth; naturally occurring phosphatides, such as soybean lecithin, esters or partial esters derived from fatty acids; hexitol anhydrides, such as sorbitan monooleate; and condensation products of these partial esters with ethylene oxide, such as polyoxyethylene sorbitan monooleate. In some embodiments, the emulsion also contains sweetening and flavoring agents. In various cases, syrups and elixirs are formulated with sweetening agents, such as glycerol, sorbitol or sucrose. Such compositions, in some cases, also contain a demulcent, a preservative, a flavoring or a coloring agent.

Additionally, in various embodiments, the pharmaceutical compositions are sterile injectable preparation, such as a sterile injectable aqueous emulsion or oleaginous suspension. This emulsion or suspension may be formulated by a person of ordinary skill in the art using those suitable excipients, such as dispersing or wetting agents and suspending agents, including those mentioned above. The sterile injectable preparation may also be a sterile injectable solution or suspension in a non-toxic parenterally acceptable diluent or solvent, such as a solution in 1,2-propane-diol.

In some cases, the sterile injectable preparation is prepared as a lyophilized powder. Among the acceptable vehicles and solvents that may be employed are water, Ringer's solution, and isotonic sodium chloride solution. In addition, sterile fixed oils may be employed as a solvent or suspending medium. For this purpose any bland fixed oil may be employed including synthetic mono- or diglycerides. In addition, fatty acids (e.g., oleic acid) may likewise be used in the preparation of injectables.

To obtain a stable water-soluble dose form of a pharmaceutical composition, a pharmaceutically acceptable salt of a compound described herein is dissolved in an aqueous solution of an organic or inorganic acid, such as 0.3 M solution of, e.g., succinic acid or citric acid. If a soluble salt form is not available, the compound is dissolved in a suitable co-solvent or combination of co-solvents. Examples of suitable co-solvents include alcohol, propylene glycol, polyethylene glycol 300, polysorbate 80, glycerin and the like in concentrations ranging from about 0 to about 60% of the total volume. In one embodiment, the active compound is dissolved in DMSO and diluted with water.

In various embodiments, the pharmaceutical composition is a solution of a salt form of the compound in an appropriate aqueous vehicle, such as water or isotonic saline or dextrose solution. Also contemplated are compounds which have been modified by substitutions or additions of chemical or biochemical moieties which make them more suitable for delivery (e.g., increase solubility, bioactivity, palatability, decrease adverse reactions, etc.), for example by esterification, glycosylation, PEGylation, etc.

In some embodiments, the compounds described herein are formulated for oral administration in a lipid-based formulation suitable for low solubility compounds. Lipid-based formulations can generally enhance the oral bioavailability of such compounds. As such, pharmaceutical compositions comprise a therapeutically or prophylactically effective amount of a compound described herein, together with at least one pharmaceutically acceptable excipient selected from the group consisting of medium chain fatty acids and propylene glycol esters thereof (e.g., propylene glycol esters of edible fatty acids, such as caprylic and capric fatty acids) and pharmaceutically acceptable surfactants, such as polyoxyl 40 hydrogenated castor oil.

In some embodiments, cyclodextrins are added as aqueous solubility enhancers. Exemplary cyclodextrins include hydroxypropyl, hydroxyethyl, glucosyl, maltosyl and maltotriosyl derivatives of α-, β-, and γ-cyclodextrin. A specific cyclodextrin solubility enhancer is hydroxypropyl-β-cyclodextrin (HPBC), which may be added to any of the above-described compositions to further improve the aqueous solubility characteristics of the compounds of the embodiments. In one embodiment, the composition comprises about 0.1% to about 20% hydroxypropyl-o-cyclodextrin, about 1% to about 15% hydroxypropyl-(β-cyclodextrin, and from about 2.5% to about 10% hydroxypropyl-o-cyclodextrin. The amount of solubility enhancer employed will depend on the amount of the compound of the invention in the composition.

Methods of Treatment

Methods disclosed herein include methods of inhibiting a bacterial infection in a cell, such as an infection due to *Staphylococcus aureus*, methicillin resistant *S. aureus, Bacillus anthracis, Escherichia coli, Shigella flexneri*, and *Salmonella typhimurium*. In some cases, the bacteria are MRSA.

High Throughput Screening for Inhibitors of Siderophore Biosynthesis Derived from Natural Product Extracts.

A marine microbial-derived natural product extract (NPE) library was used to identify inhibitors of NIS synthetases in *S. aureus* and *B. anthracis*. The majority of currently marketed drugs are derived from natural products,[33,34] and the marine environment in particular is thought to be an underexplored source of novel chemical structures.[35] An enzymatic high throughput assay was developed specific to SbnE and AsbA, and adapted to a malachite green reporter system.[36-38] The assay was then queried against a library of 19,855 marine microbial-derived NPEs to identify inhibitors of enzyme activity (FIG. 2). The NPEs in this library are primarily from marine-derived microorganisms collected in various areas worldwide. Screening SbnE and AsbA in parallel limited the number of false positives and provided a convenient method for prioritization of active extracts. Two rounds of screening yielded 33 strains with greater than 70% inhibition against SbnE at 7.5 μg/mL and 22 strains with extracts showing greater than 50% inhibition against AsbA at 75 μg/mL (FIG. 2). The higher frequency and activity of extracts against SbnE is likely due to the lower enzyme concentration (25 nM) compared to the AsbA (100 nM) utilized in screening. These were the lowest enzyme concentrations for each respective assay that produced a response fit for screening (FIG. 7). Low enzyme concentrations were desired to maximize the likelihood of detecting extracts possessing low-abundance bioactive components.

Among active extracts, *Streptomyces tempisquensis* was of particular interest due to its high activity against both SbnE (95.9%) and AsbA (90.2%). The strain was originally isolated from sediments collected in Playa Grande, Costa Rica (−85°49'39.8", 10°18'39.8") near Las Baulas National Marine Park.

Isolation and Structural Elucidation of the Baulamycins (6-7).

An iterative bioassay guided C18 fractionation and subsequent RP-18 HPLC purification yielded two novel bioactive molecules (FIG. 3), baulamycins A (BmcA, 6) and B (BmcB, 7), whose structures are consistent with biogenesis from a type I polyketide synthase pathway. BmcA (6) was purified as a light yellow amorphous solid and possesses a molecular formula of $C_{28}H_{48}O_6$ as suggested by HRAPCIMS based on $[M+H]^+$ ion peak at m/z 481.3530. The $^1H$ and $^{13}C$ NMR data, recorded in $CD_3OD$ indicated the polyketide nature of 6 and indicated the presence of at least three hydroxyl group bearing methines with chemical shifts at δ 4.47 (76.5), 4.01 (73.3) and 3.69 (72.5). Further analysis of the $^1H$ NMR spectrum of 6 identified 12 aliphatic protons in the region of $\delta_H$ 0.95-2.77 and six methyl groups at $\delta_H$ 0.77 (d), 0.83 (d), 0.86 (d), 0.88 (d), 1.02 (t) and 1.06 (d). The $^{13}C$ NMR and HSQCAD spectra revealed the presence of four quaternary carbons at $\delta_C$ 148.6 (an aromatic carbon), 159.1 (two chemically equivalent aromatic carbons) and at $\delta_C$ 218.7 (a carbonyl carbon). The gCOSY correlations between two equivalent aromatic protons with a signal at $\delta_H$ 6.33, 6.15 and HMBCAD correlation between $\delta_H$ 6.33, 6.15 to the equivalent carbons at $\delta_C$ 159.1, 105.9 and carbon at $\delta_C$ 148.6 clearly suggested the presence of resorcinol moiety (Table 1). Similarly, the connectivity from C-1 to C-17 was confirmed by an array of COSY and HMBC couplings in both $CD_3OD$ and DMSO-$d_6$ to construct a 17-carbon aliphatic straight chain with a characteristic carbonyl carbon at $\delta_C$ 218.7. In addition, COSY correlation was observed between H-1 and protons at C-2 along with their HMBC connection to C-3 suggesting an ethyl-ketone terminus for molecule 6. Moreover, the COSY and HMBC correlations indicated the branching of aliphatic chain through a methyl group at C-4 ($\delta_H$ 2.77, $\delta_C$ 44.6), C-6 ($\delta_H$ 1.42, $\delta_C$ 29.1), C-8 ($\delta_H$ 1.53, $\delta_C$ 30.9), and C-16 ($\delta_H$ 1.38, $\delta_C$ 26.6) positions. The position of the hydroxyl group at C-11 and C-13 were consistent with the distinctive $^1H$ and $^{13}C$ chemical shifts at $\delta_H$ 3.69, $\delta_C$ 72.5 and $\delta_H$ 4.01, $\delta_C$ 73.3, respectively. Furthermore, HMBC showed a correlation from H-1' ($\delta_H$ 4.47) to C-2' ($\delta_C$ 148.6) along with its contiguous COSY correlation to H-14 ($\delta_H$ 1.88) indicating a branch-point for the aliphatic chain at C-14 through a pendant attachment of 5'-(hydroxymethyl)-resorcinol moiety to complete the structure of BmcA (6) (Table 1)

TABLE 1

NMR spectroscopic data for baulamycins A (6) and B (7) in $CD_3OD$ at 700 MHz.

| | Baulamycin A (6) | | | | Baulamycin B (7) | |
|---|---|---|---|---|---|---|
| | $\delta_C$ | $\delta_H$, multi (J in Hz) | COSY | HMBC | $\delta_C$ | $\delta_H$ |
| 1 | 35.1 | 2.57, dp | 2" | 1, 2", 2 | 27.4 | 2.15 |
| | | 2.49, dp | 2" | 1, 2", 2 | | |
| 2 | 7.8 | 1.02, t (6.9, 7.3) | 1" | 1, 1", 2 | | |
| 3 | 218.7 | | | | 214.6 | |
| 4 | 44.6 | 2.77, ddq (3.2, 6.7, 8.0) | 3 | 1, 3, 19 | 43.9 | 2.70 |
| 5 | 41.7 | 1.73, ddd (3.2, 5.0, 11.0) | 2 | 1, 2, 4 | 41.8 | 1.72, 0.97 |
| | | 0.98, ddd (6.7, 8.0, 11.0) | 4 | | | |
| 6 | 29.1 | 1.42, ddddq (3.0, 3.2, 5.0, 13.0) | 3, 5 | 6, 18 | 29.2 | 1.44 |
| 7 | 46.3 | 1.22, ddd (3.0, 11.0, 13.0) | 6 | 17, 18 | 46.0 | 1.22 |
| | | 0.95, ddd (3.2, 5.0, 11.0) | 3 | 17, 18 | | 0.95 |
| 8 | 30.9 | 1.53, ddddq (3.0, 5.0, 8.5, 13.0) | 5, 7 | 5, 7, 17 | 31.0 | 1.55 |
| 9 | 33.0 | 1.33, dddd (3.0, 3.0, 10.6) | 6, 8 | 9, 17 | 33.4 | 1.34 |
| | | 1.19, dddd (8.5, 9.0, 10.6) | 6, 8 | 7, 5 | | 1.21 |
| 10 | 35.4 | 1.41, dddd (9.0, 11.0, 11.6) | 7, 9 | 11, 17 | 35.1 | 1.40 |
| | | 1.39, dddd (3.0, 4.0, 11.6) | 7, 9 | | | 1.38 |
| 11 | 72.5 | 3.69, dddd (8.0, 11.0, 12.0) | 8, 10 | 7, 8.11 | 72.2 | 3.72 |
| 12 | 40.6 | 1.79, ddd (8.0, 7.2, 11.0) | 9, 11 | | 40.2 | 1.80, 1.50 |
| | | 1.55, ddd (3.1, 3.2, 11.0) | | | | |
| 13 | 73.3 | 4.01, dt (9.9, 3.4) | 10, 12 | 1', 9, 13 | 73.0 | 3.99 |
| 14 | 48.5 | 1.88, ddq (7.7, 7.0) | 11, 13 | 1', 11, 14 | 48.7 | 1.80 |
| 15 | 37.3 | 1.21, m | 12, 14 | | 37.0 | 1.20 |
| 16 | 26.6 | 1.38, m | 13, 15 | | 26.6 | 1.38 |
| 17 | 22.5 | 0.83, d (6.5) | 14 | 13, 14 | 22.4 | 0.82 |
| 18 | 23.3 | 0.77, d (6.5) | 14 | 13, 14 | 23.3 | 0.77 |

TABLE 1-continued NMR spectroscopic data for baulamycins A (6) and B (7) in CD$_3$OD at 700 MHz.

| | Baulamycin A (6) | | | | Baulamycin B (7) | |
|---|---|---|---|---|---|---|
| | $\delta_C$ | $\delta_H$, multi (J in Hz) | COSY | HMBC | $\delta_C$ | $\delta_H$ |
| 19 | 20.3 | 0.86, d (6.6) | 6 | 5, 6, 7 | 20.1 | 0.85 |
| 20 | 20.5 | 0.88, d (6.5) | 4 | 3, 4, 5 | 20.2 | 0.88 |
| 21 | 17.9 | 1.06, d (6.9) | 2 | 1, 2, 3 | 18.0 | 1.01 |
| 1' | 76.5 | 4.47, d (7.0) | 12 | 2', 3', 8, 13, 11 | 76.4 | 4.50 |
| 2' | 148.6 | | | | 148.2 | |
| 3' | 105.9 | 6.33, d (2.2) | 5' | 1', 2', 3', 4', | 106.1 | 6.35 |
| 4' | 159.1 | | | | 158.5 | |
| 5' | 101.9 | 6.15, t (2.2) | 3' | 3', 4' | 101.8 | 6.16 |

BmcA (6) has seven stereocenters with three hydroxyl bearing carbons, three methyl bearing carbons and a 2-methylpropane containing stereocenter. Initial attempts were made to obtain absolute stereochemical information through chemical manipulations for at-least hydroxyl bearing chiral centers. However, the relatively low yield of baulamycins rendered this approach impractical. Therefore, a nondestructive J based configuration analysis (JBCA)[39] was employed to propose the relative configuration of BmcA (6).[40-42] The $^3J_{H-H}$, $^2J_{C-H}$, and $^3J_{C-H}$ values were calculated using a combination of phase sensitive double quantum filtered (PS-DQF)-COSY, homonuclear 2D J spectroscopy (HOMO2DJ), gradient- and sensitivity-enhanced hetero (ω1) half filtered TOCSY (HETLOC-gse) and heteronuclear 2D J (HET2DJ) spectral analyses (FIGS. 13-15).

Figure 3:
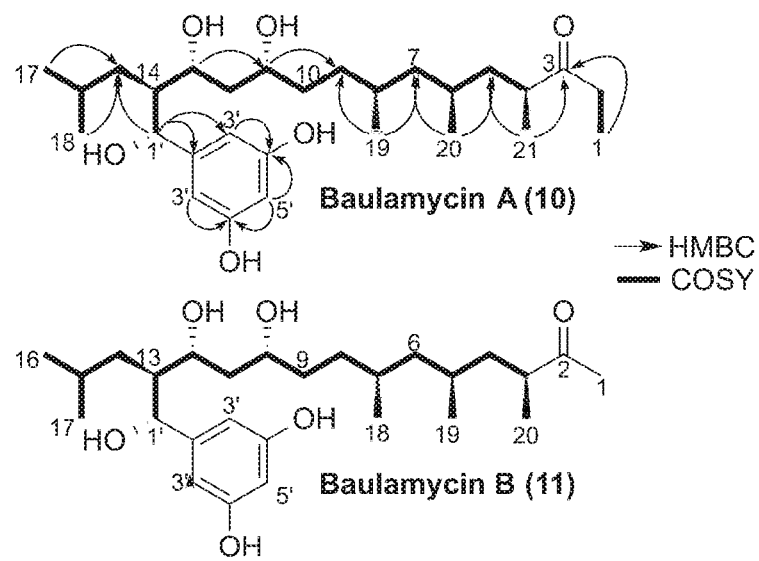
FIG. 3. Planar structure of baulamycins A (6) and B (7) showing COSY correlation with bold bonds and HMBC correlations with arrow.
Figure 4:
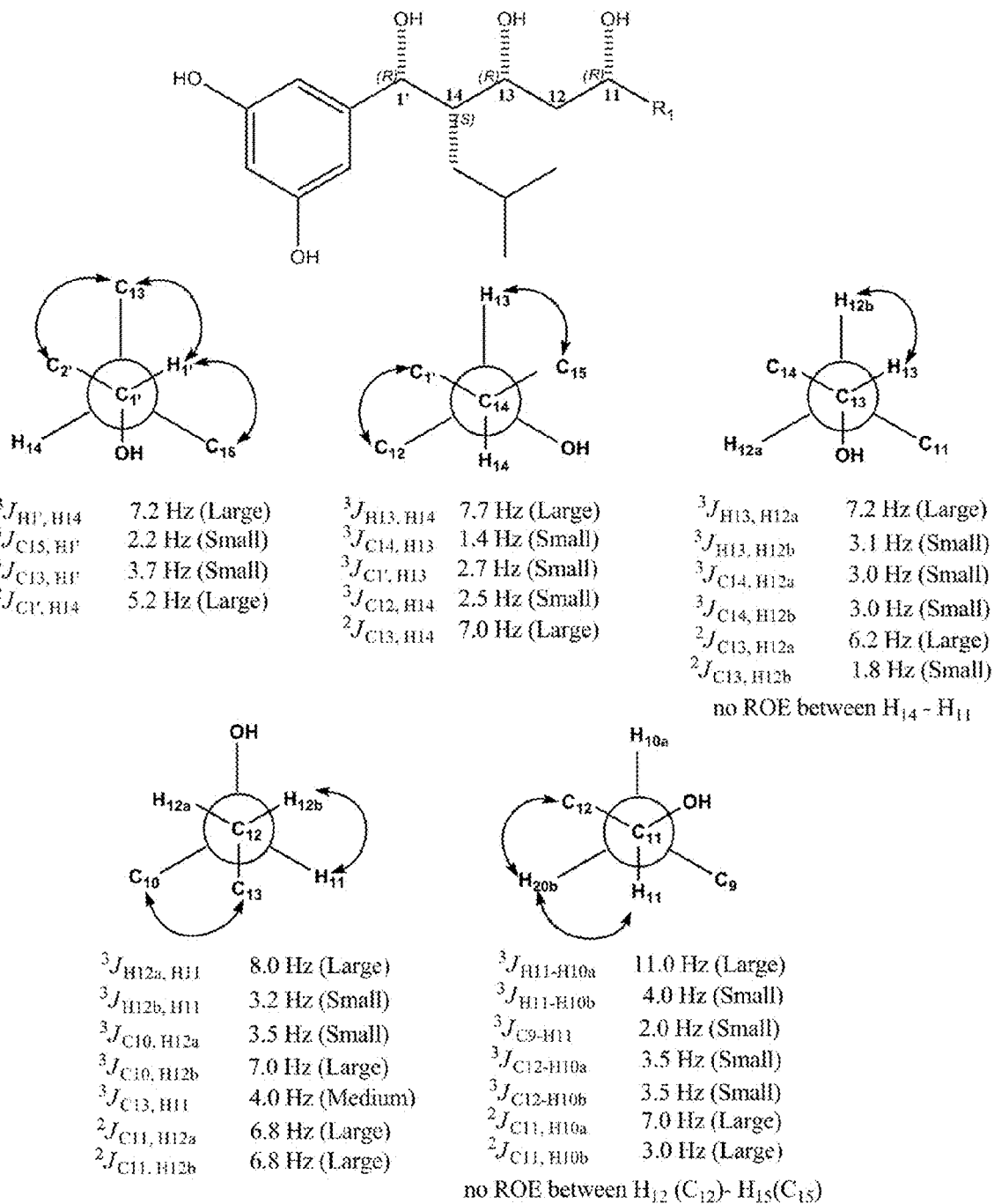
FIG. 4: H—H, C—H coupling values and relative configuration determined for C1'-C11. Arrows showing ROESY correlations.

The relative configurations of stereocenters (C11-C13-C14-C1') in 6 established by JBCA are as follows. At the C1'-C14 axis, a large coupling constant $^3J_{H1'-H14}$~7.2 Hz and $^2J_{C1'-H14}$~5.2 Hz, inferred their anti and gauche orientations, respectively[39] (FIG. 4). For the C14-C13 bond, the large $^3J_{H14-H13}$~7.7 Hz suggested anti orientation, which was also supported by the observed ROESY correlations. An additional large $^2J_{C13-H14}$~7.0 Hz was indicative of the gauche orientation between O-13 and H-14[39] (FIG. 4). Further, the HOMO2DJ spectrum was sliced at $\delta_H$ 4.01 (H-13) suggesting a large coupling constant between H13-H12a and a small value between H13-H12b indicative of anti and gauche orientations, respectively (FIG. 4). For the C12-C11 moiety, the HOMO2DJ spectrum was sliced at $\delta_H$ 3.69 (H-11) to yield $^3J_{H12a-H11}$~8.0 Hz and $^3J_{H12a-H11}$~3.2 Hz suggesting anti and gauche orientation, respectively (FIG. 4). Furthermore, large coupling constants were recorded for $^2J_{C11-H12a}$~6.8 Hz and $^2J_{C11-H12b}$~7.2 Hz clearly indicating gauche orientations between O-11 and H-12a/H-12b[39] (FIG. 4). Moving down the axis over C11-C10 moiety, large coupling constant between H-11/H-10a, H-11/H10b and C11/H10a suggested gauche orientation between O-11 and H-10a. Hence, the relative configurations at C1', C14, C13 and C11 were proposed as 1'R*, 14S*, 13R* and 11R*, respectively (FIG. 3).

Figure 5:
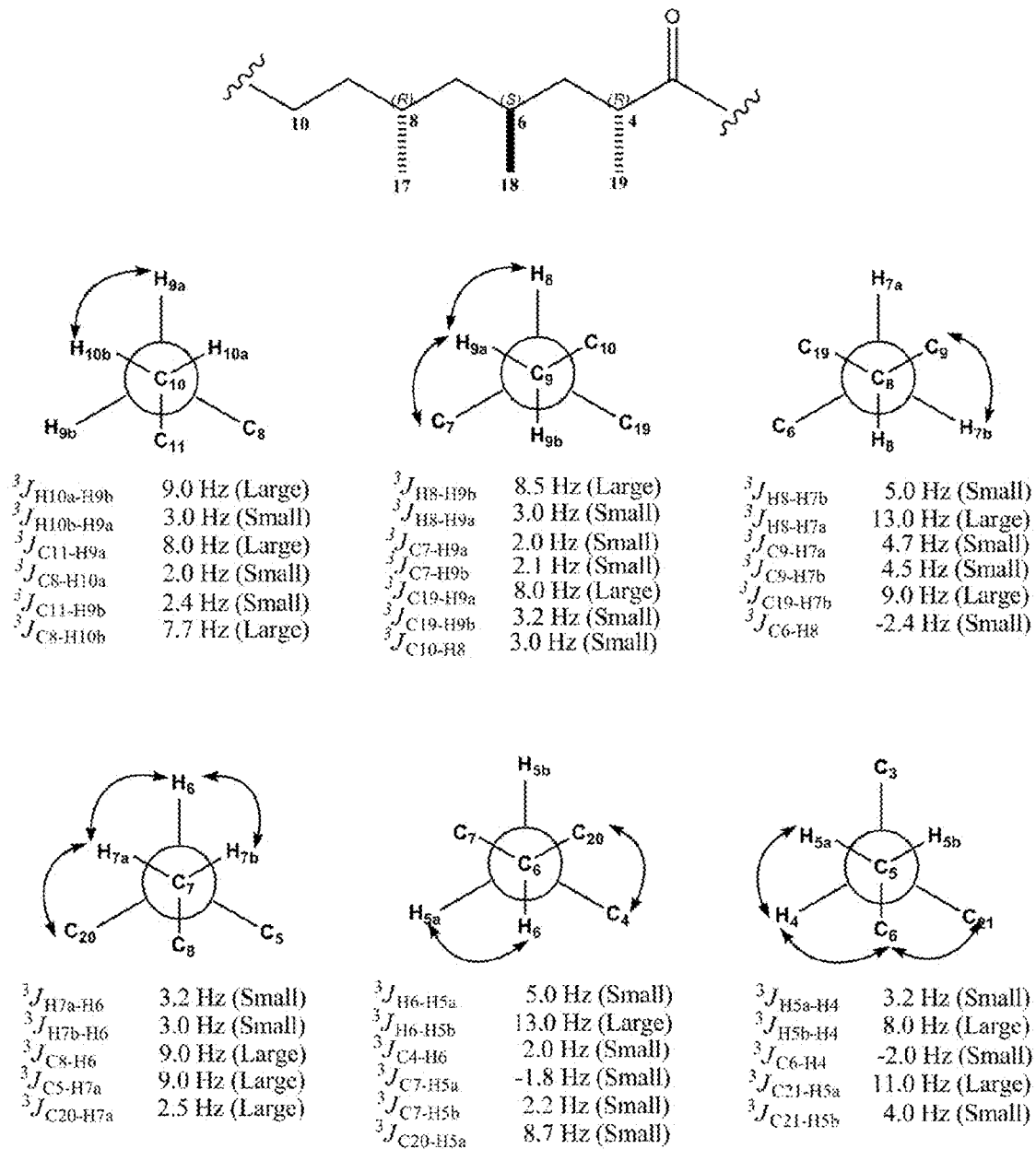
FIG. 5: H—H, C—H coupling values and relative configuration determined for C10-C4. Arrows showing ROESY correlations.

Establishment of the relative orientation of protons associated with non-chiral C-10 and C-9 was necessary to measure stereochemistry of subsequent chiral carbons (C8-C4). Each of the HOMO2DJ and PS-DQF-COSY spectra was sliced at $\delta_H$ 1.41, 1.39 (H-10a, H-10b) and $\delta_H$ 1.19, 1.33 (H-10a, H-10b), respectively. The slicing provided large coupling constants between H-10a/H-9b and small between H-10a/H-9a suggesting anti and gauche orientations, respectively (FIG. 5). Correspondingly, for the C9-C8 axis, calculations yielded $^3J_{H9b-H8}$~8.5 Hz (large) and $^3J_{H9a-H8}$~3.0 Hz (small) indicating anti and gauche conformations, respectively (FIG. 5). Furthermore, the ROESY correlations and small coupling values obtained from $^3J_{C7-H9a}$~2.0 Hz and $^3J_{C-H9b}$~2.1 Hz the gauche orientations between C7 and H-9a/H-9b facilitating assignment of the relative conformation of H-9a and H-9b at C9 (FIG. 5).

For C9-C8 axis, the observation of a large $^3J_{H8-H9b}$ (8.5 Hz) and $^3J_{C19-H9a}$ (8.0 Hz) values indicated that H-8 and H9b as well as C-19 and H-9a are in the anti orientation. The relative configuration at C8 was established to be R* according to the ROE between H-8 and H-9a (FIG. 5). For the C8/C7 bond, the relationship of C19/H-7b was revealed as anti based on a large $^3J_{C19-H7b}$~9.0 Hz value. Another large coupling value ($^3J_{H7a-H8}$~13.0 Hz) and corresponding small coupling value between C6 and H-8($^J_{C6-H8}$~2.4 Hz) led us to assign the relative conformation of H-7a and H-7b at C7 (FIG. 5). For the C7/C6 bond, the observation of small coupling values ($^3J_{H7a-H6}$~3.0 Hz and $^3J_{7b-H6}$~3.2 Hz) along with apparent ROE between H-6 and H-7a/H-7b suggested gauche orientation between H-6 and H-7a/H7b, establishing relative configuration at C6 as S* (FIG. 5).

For C6 and C5, a large $^3J_{H6-H5b}$ value (~13.0 Hz) and small $^3J_{H6-H5a}$ value (~5.0 Hz) revealed that H-6/H-5b and H-6/H-5a possess anti and gauche relationships, respectively. Additionally, small $^3J_{C4-H6}$~2.0 Hz and $^3J_{C7-H5a}$~-1.8 Hz values as well as observed ROE between H-5a and H-6 revealed the relative conformation of H-5a and H-5b at C5 (FIG. 5). For the C5/C4 axis, a large $^3J_{H5b-H4}$~8.0 Hz and small $^3J_{H5a-H4}$~3.2 Hz coupling values was obtained from HOMO2DJ and PS-DQF-COSY indicating anti and gauche conformations, respectively. In addition, an anti orientation of the C21 and H-5a atoms was deduced from the large $^3J_{C21-H15a}$~11.0 Hz value obtained from HETLOC-gse spectrum. Further, in ROESY spectrum, ROEs between H-5a/H-4, H-4/H-6 and H-6/H-21 was observed. Taking these data into consideration, the relative configuration at C4 was proved to be R*. Therefore, the relative configuration for C10-C4 moiety was anticipated as 8R*, 6S* and 4R*, respectively, in BmcA (6).

BmcB (7) was isolated by RP-18-HPLC from the same C18 fraction containing compound 6. The HRESIMS of the molecule provided a molecular formula of $C_{27}H_{46}O_6$ showing a [M+H]$^+$ ion peak at 467.3171. Moreover, baulamycin B (7) had high structural similarity to 6, as evidenced by nearly identical $^1$H and $^{13}$C NMR chemical shifts when measured in CD$_3$OD (Table 1). However, it displayed a subtle difference towards the carbonyl terminus, revealing the absence of terminal ethyl protons and substituting with a terminal methyl singlet at $\delta_H$ 2.18 in the 1H NMR spectrum of compound 7. The relative stereochemistry from C1'-C10 and C5-C3 were proposed to be identical to those of 6 on the basis of highly comparable NMR spectroscopy data.

Assessment of the In Vitro Biological Activity of Compounds Against Purified NIS Enzymes.

Figure 6:
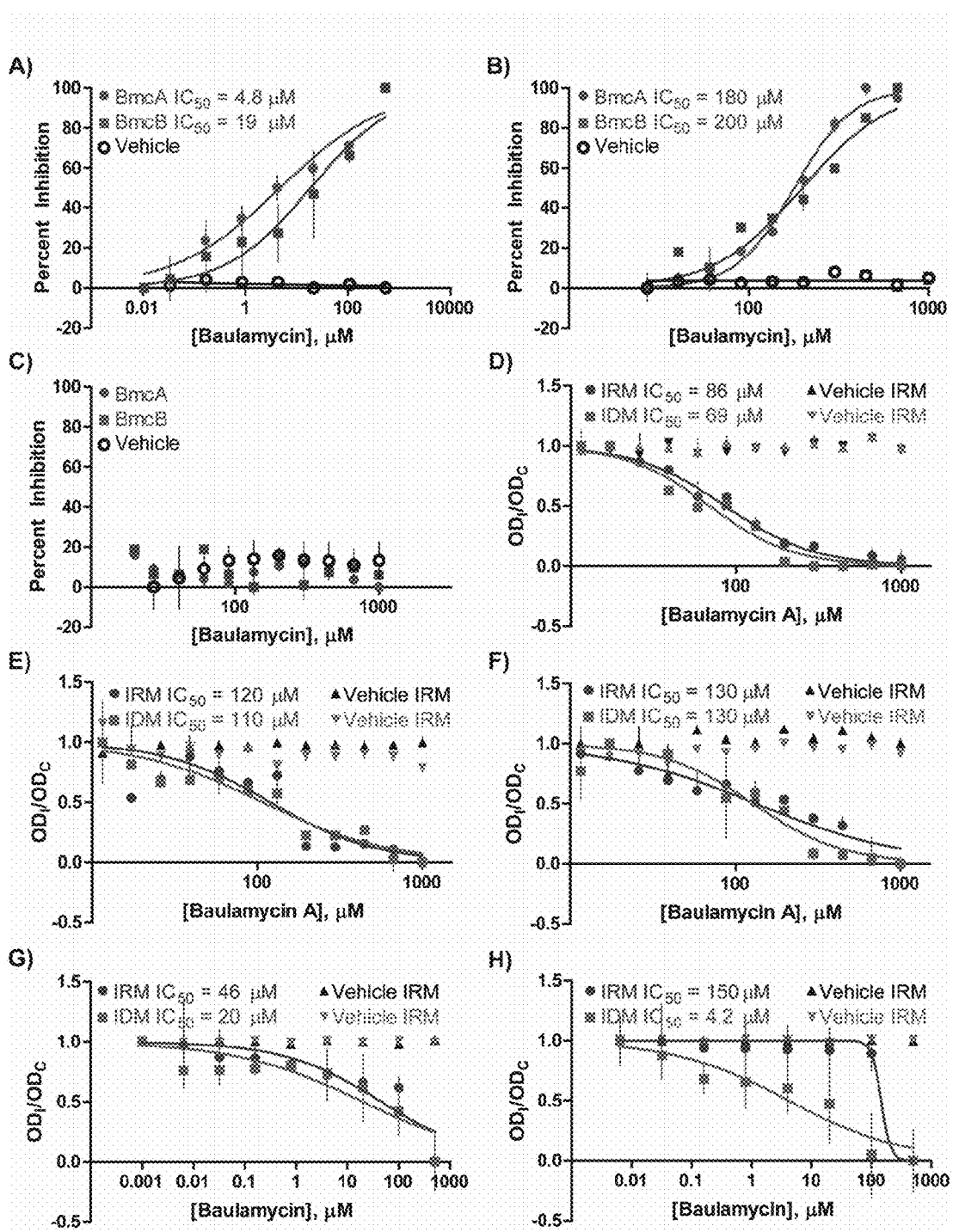
FIG. 6. (A-C) In vitro bioactivities against purified enzyme recorded for BmcA and BmcB against the NIS synthetase (A) SbnE, (B) AsbA, or (C) AsbB. (D-H) BmcA inhibition against live cultures of microbial strains (D) S. aureus (Newman), (E) B. anthracis (Sterne 34F2), F) MRSA (USA 300), G) S. flexneri, or (H) E. coli (MC 1061) in iron-depleted (IDM) or iron-rich (IRM) media. The y-axis represents a comparison of the optical densities of inhibitor- (ODI) and DMSO control-treated (ODC) cultures. Assays were conducted in duplicate due to the current limited availability of the baulamycins.
Figure 7:
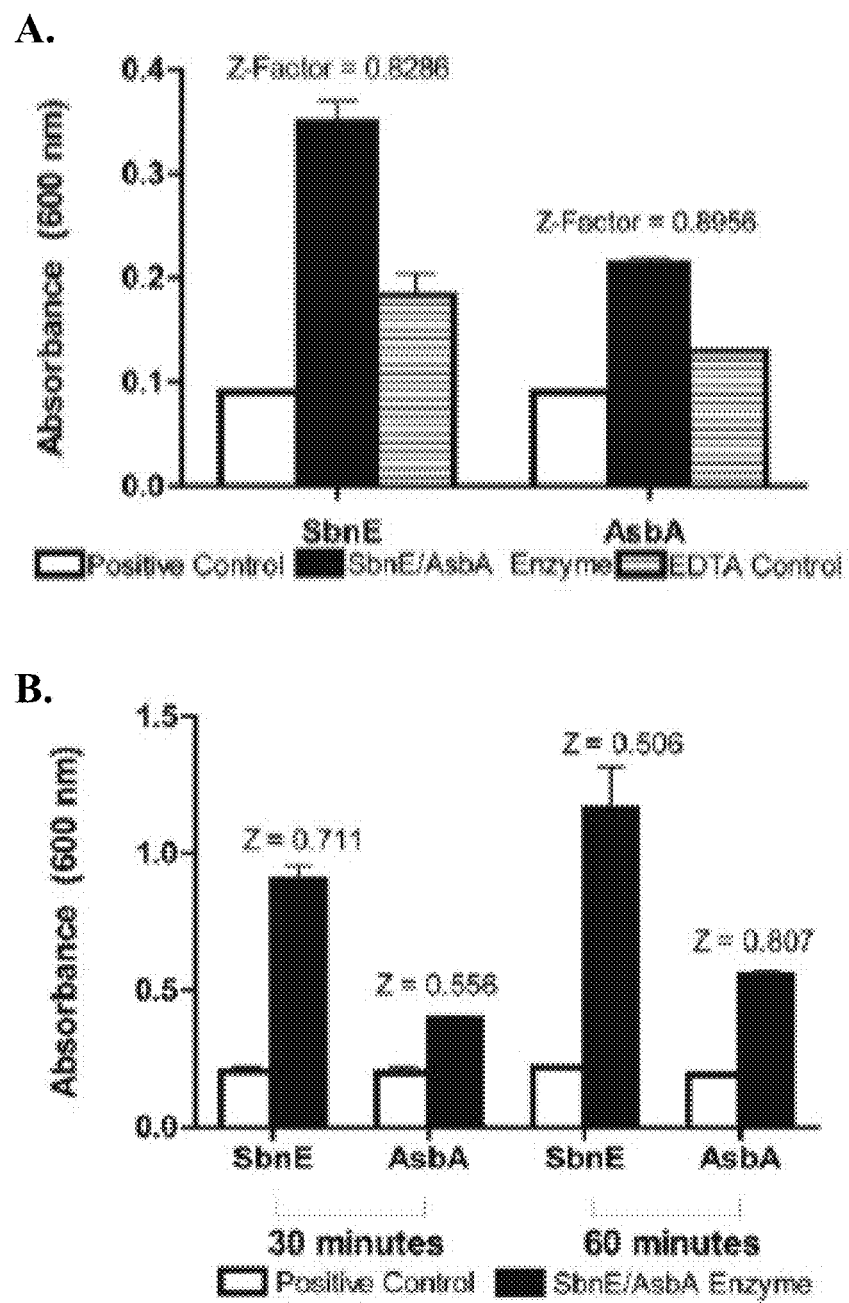
FIG. 7 (A-E) shows the development of an NIS synthetase assay for screening. (a) Testing of the fitness of the NIS hydroxamate-formation assay for HTS. (b) Optimization of the incubation time for SbnE and AsbA reactions. (c) The malachite green assay tailored to NIS synthetases SbnE and AsbA. (d) Optimization of the development time for SbnE and AsbA after quenching with the malachite green solution. (e) Optimization of enzyme concentration for the high throughput assays.
Figure 7:
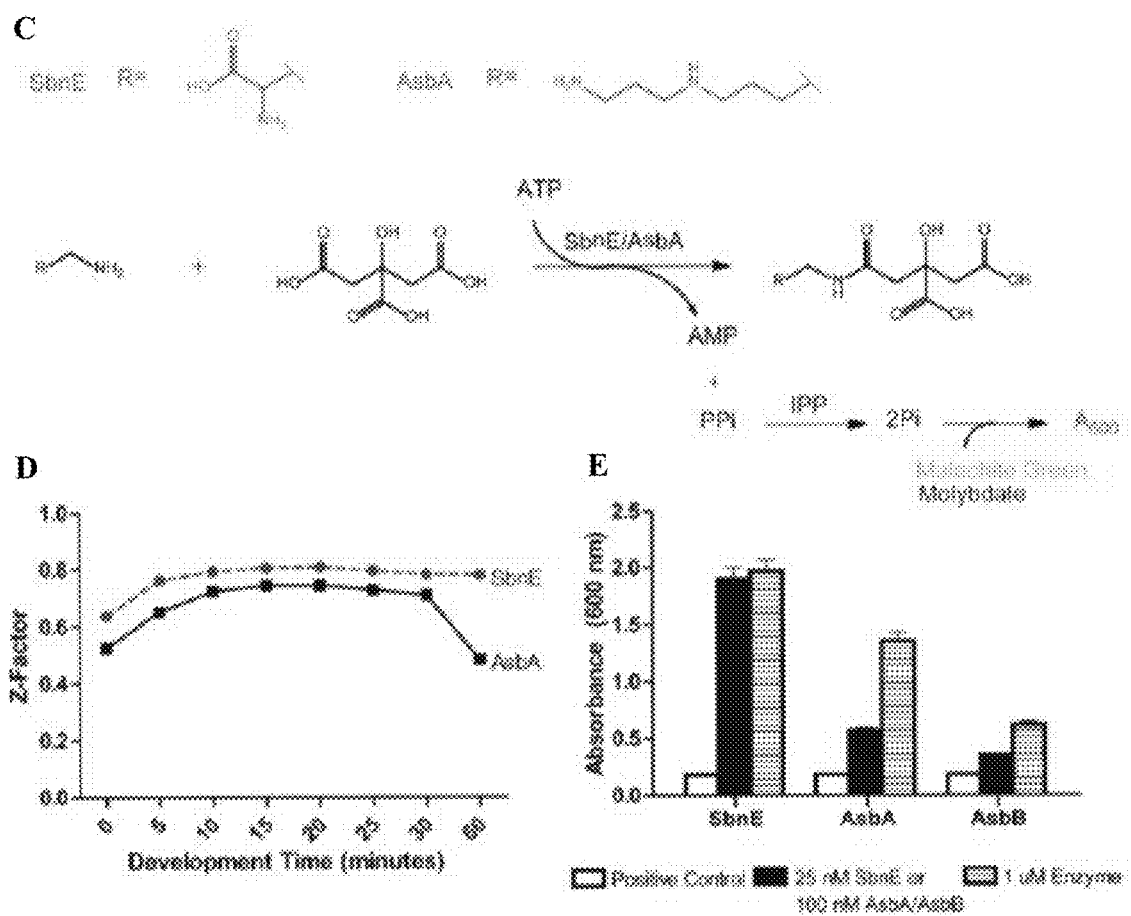

The malachite green-based bioassay was next employed to assess the dose response of novel compounds BmcA (6) and BmcB (7) against purified SbnE and AsbA (Table 2). Both compounds exhibited in vitro bioactivity against SbnE, with $IC_{50}$ values of 4.8 µM and 19 µM for BmcA and BmcB, respectively (FIG. 6A). Inhibition was also observed against AsbA, with $IC_{50}$ values of 180 µM and 200 µM for BmcA and BmcB, respectively (FIG. 6B). The significant difference in apparent inhibition is likely due to the different enzyme concentrations used in the dose response assays, 25 nM for SbnE and 100 nM for AsbA. The assays were originally optimized at these enzyme concentrations to maximize the detection of extracts containing low levels of bioactive components during screening.

TABLE 2

| Enzymatic Target | NIS Synthetase Classification | Associated Microbial Strain | Associated Siderophore | BmcA $IC_{50}$ (µM) | BmcB $IC_{50}$ (µM) |
| --- | --- | --- | --- | --- | --- |
| SbnE | Type A | S. aureus | Staphyloferrin B | 4.8 | 19 |
| AsbA | Type A | B. anthracis | Petrobactin | 180 | 200 |
| AsbB | Type C | B. anthracis | Petrobactin | >1000 | >1000 |

As a next step to address whether the baulamycins selectively inhibited type A over other NIS synthetase subfamilies, the activity of both compounds against the petrobactin biosynthetic type C NIS synthetase AsbB was explored. While type A NIS synthetases prefer citric acid as a substrate, type C enzymes generally utilize citric or succinic acid derivatives often found as complex intermediates within their respective siderophore biosynthetic pathways.[31] In the petrobactin pathway, AsbB catalyzes condensation of a second molecule of spermidine with either N8-citryl-spermidine (3) or N1-(3,4-DHB)-N8-citryl spermidine (4).[30] Interestingly, recent work in our laboratory also demonstrates AsbB to be more flexible in substrate selection and capable of partial compensation for AsbA activity in vitro.[30] Despite these findings, dose response studies revealed inhibition against AsbB to be negligible for both BmcA and BmcB (FIG. 6C). These data indicate that both natural products are more potent in vitro against the type A NIS synthetases SbnE and AsbA than the type C subfamily member AsbB.

Initial Enzyme Mechanism of Inhibition Studies.

To investigate how the more potent of the two compounds, BmcA (6), inhibits SbnE and AsbA enzymatic activity, NIS synthetase ATP turnover was monitored using a previously described 2-amino-6-mercapto-7-methylpurine ribonucleoside (MESG) kinetic pyrophosphate detection assay.[43,44] These experiments were conducted by varying a single substrate and holding remaining reaction components at a constant saturating level in the presence and absence of inhibitor. The resulting double reciprocal (Lineweaver-Burk) plots confirmed that kinetic parameters closely matched previously reported values for both enzymes against varied citrate concentrations (Table S1).[20,30] The plots suggested that BmcA inhibits both enzymes in a reversible, competitive manner with respect to citric acid, the corresponding polyamine, and ATP. Although kinetic assays were only conducted with BmcA due to its higher potency and availability (obtained in substantially higher yield from Streptomyces tempisquensis), it is reasonable to expect that BmcB also possesses these inhibition patterns.

A replot of slopes derived from the Lineweaver-Burk plot versus inhibitor concentration also enabled an initial investigation into the inhibition constants ($K_i$ values) for BmcA against both enzymes (Table S1).[45] Interestingly, the inhibitor constants were lowest for citric acid (SbnE: 50 µM; AsbA: 110 µM) followed by the polyamine substrate (SbnE: 210 µM; AsbA: 170 µM) and ATP (SbnE: 680 µM; AsbA: 230 µM). This is surprising given the polar nature of citric acid in comparison to the baulamycins. The explanation for this likely depends on the structure and substrate binding sites in the proteins. Although no structural studies have yet been conducted with SbnE or AsbA, the crystal structures of AsbB and the achromobactin type A NIS synthetase in Pectobacterium chrysanthemi have been determined.[30,46] Both reveal a single active site that houses substrates and intermediates during catalysis. Elucidation of the differences in the structures of SbnE, AsbA, and these other NIS synthetases could shed light on the exact mechanism of inhibition exerted by the baulamycins and their complete lack of activity against AsbB. Efforts to acquire X-ray crystal structures of both SbnE and AsbA in the presence and absence of baulamycin compounds are expected in due course. Additionally, mutagenesis and selection of S. tempisquensis should improve the yield of the baulamycins, enabling a sufficient amount of these molecules for comprehensive kinetic analysis.

Assessment of Biological Activity Against Microbial Cultures.

Since siderophore biosynthesis is required for bacterial survival in iron-limited environments, a selective siderophore synthetase inhibitor would be expected to limit growth only under these conditions. Therefore, bacterial growth in both iron-depleted (IDM) and iron-rich (IRM) media conditions in the presence of 6 and 7 was assessed. Live culture studies were also conducted to demonstrate the ability of both natural products to penetrate the bacterial cell wall, an established advantage of natural products over many synthetic chemicals.[47] However, due to the extremely low yield of the baulamycins from S. tempisquensis, experiments could only be completed in duplicate and the following studies represent an initial assessment of microbial culture bioactivity.

BmcA was found to inhibit growth of S. aureus (Newman) in both iron-depleted ($IC_{50}$=69 µM) and iron-rich ($IC_{50}$=86 µM) conditions, (FIG. 6D, Table 3). Similar inhibition was observed with B. anthracis (Sterne 34F2) under iron-depleted ($IC_{50}$=110 µM) and iron-rich ($IC_{50}$=120 µM) conditions (FIG. 6E, Table 3), suggesting possible secondary targets in the cell. In agreement with in vitro findings against purified enzyme, BmcB was significantly less potent against S. aureus (Newman) and B. anthracis (Sterne 34F2).

TABLE 3

| Microbial Strain | Classification | Targeted Siderophore Pathway | Associated NIS Synthetase | BmcA IRM IC$_{50}$ (μM) | BmcA IDM IC$_{50}$ (μM) |
| --- | --- | --- | --- | --- | --- |
| S. aureus (Newman) | Gram-positive | Staphyloferrin B | SbnE (A), SbnC (B), SbnF (C) | 86 | 69 |
| MRSA (USA 300) | Gram-positive | Staphyloferrin B | SbnE (A), SbnC (B), SbnF (C) | 130 | 130 |
| B. anthracis (Sterne 34F$_2$) | Gram-positive | Petrobactin | AsbA (A), AsbB (C) | 120 | 110 |
| S. typhimurium | Gram-negative | Aerobactin | IucA (A), IucC (C) | >1000 | >1000 |
| E. coli (MC 1061) | Gram-negative | Aerobactin | IucA (A), IucC (C) | 150 | 4.2 |
| S. flexneri (BS103) | Gram-negative | Aerobactin | IucA (A), IucC (C) | 46 | 20 |

The potency of BmcA against a clinically isolated MRSA strain (USA 300). Similar to *S. aureus* (Newman) and *B. anthracis* (Sterne 34F2) was tested. BmcA also inhibited MRSA (USA 300) in iron-depleted (IC$_{50}$=130 μM) and iron-rich (IC$_{50}$=130 μM) conditions (FIG. 6F, Table 3), again suggesting secondary cellular targets.

Encouraged by the potency of these compounds on *S. aureus* and *B. anthracis* strains, inhibition of the more active BmcA was tested on additional microorganisms possessing NIS synthetase siderophore biosynthetic pathways. Aerobactin was the first discovered siderophore to be assembled by an NIS synthetase system.[31,48] It contributes to the virulence of a multitude of bacteria, including *E. coli*, and multiple species of *Salmonella, Yersinia*, and *Shigella*.[31,49] The pathway involves the type A and C NIS synthetases IucA and IucC, respectively,[50,51] which share sequence similarity with NIS synthetases found in most other siderophore biosynthetic pathways.[31,32] Indeed, SbnE and AsbA appear to be relatives of IucA.[31,32] Furthermore, staphyloferrin B biosynthetic enzyme SbnF and petrobactin biosynthetic enzyme AsbB share sequence similarity with IucC,[31,32] collectively suggesting that the baulamycins could also inhibit aerobactin-producing bacteria. Thus, the ability of BmcA to inhibit bacterial growth of the aerobactin-producing Gram-negative strains of *Shigella flexneri, E. coli*, and *Salmonella typhimurium* in iron-depleted and iron-rich conditions was assessed (FIG. 6G,H). BmcA inhibited growth of *S. flexneri* and *E. coli* cultures in iron-depleted conditions (*S. flexneri*: IC$_{50}$=20 μM; *E. coli*: IC$_{50}$=4.2 μM) with lower potency in iron-rich conditions (*S. flexneri*: IC$_{50}$=46 μM; *E. coli*: IC$_{50}$=150 μM). Although increased potency of BmcA against *E. coli* in IDM suggests that this microbe could possess fewer nonspecific cellular drug targets. Alternatively, increased activity could be due to ability of BmcA to inhibit multiple adenylation enzymes more effectively in *E. coli*. Additional studies are required to draw any firm conclusions. While BmcA also appeared to inhibit growth of *S. typhimurium* cultures, the large standard deviations acquired during the assay led us to classify the IC$_{50}$ as above 1 mM in both iron-depleted and rich conditions. As improved access to baulamycins becomes possible, follow up studies will enable more extensive analysis of its broad-spectrum antibiotic activity.

The current analysis provides an initial assessment of the ability of BmcA to inhibit growth and demonstrates that the molecule is cell permeable. However, inhibition of all target strains under both growth conditions suggests that BmcA is acting on some additional cellular targets. Indeed, SbnE and AsbA seem to share varying levels of sequence identity with a number of enzymes in *S. aureus* and *B. anthracis*, including aminoacyl-tRNA synthetases, CoA synthetases, and fatty-acid CoA ligases in addition to critical enzymes involved in cell envelope biogenesis, inhibition of apoptosis, and spore formation.

Finally, the ability of BmcA to inhibit bacterial growth of both Gram-positive and Gram-negative strains (Table 3) classifies it as a broad-spectrum antibiotic. Although BmcB was not included in these experiments due to low production by *Streptomyces tempisquensis*, the compound is of a comparable size and possesses similar functional groups, suggesting it also could be capable of inhibiting microbial growth and infiltrating the bacterial cell wall. On the other hand, the decreased chain length and potency of BmcB suggests that longer terminal carbon chains may be important in future structure-activity relationship (SAR) studies.

A new structural class of broad-spectrum antibiotics isolated from a marine microbial derived NPE library has been identified. BmcA and BmcB inhibit siderophore biosynthesis, a crucial virulence factor associated with iron sequestration in pathogenic bacteria. Although previous studies have validated siderophore biosynthesis as an effective synthetic drug target,[8-11] the aforementioned study is the first to demonstrate its potential as a target for discovering novel chemical scaffolds. Structurally unique drugs like the baulamycins present hurdles for the bacterial development of antibiotic resistance. High throughput screening for natural product inhibitors of virulence factors including those for siderophore biosynthesis, could provide a fresh arsenal of chemical scaffolds to combat drug-resistant pathogens.

The baulamycin natural products represent promising lead structures that can be further manipulated to improve both potency and target selectivity if required. These compounds are efficacious in vitro and are capable of penetrating the cell wall to inhibit growth of bacterial cultures, including *B. anthracis*, MRSA, *S. flexneri, E. coli*, and *S. typhimurium*. The ability of the drug to inhibit growth of both Gram-positive and Gram-negative bacteria suggests its potential use as a broad-spectrum antibiotic. These growth inhibition studies further suggest that the compounds possess multiple targets in the microbial cell, likely including other adenylate-forming enzymes. This could be advantageous as drugs that impact multiple components of bacterial cells are thought to hinder pathogen acquisition of antibiotic resistance.[3] Given the simultaneous decline in antibiotic drug discovery and increase of multi-drug resistant bacteria, the baulamycins may represent an auspicious starting-point for expanding discovery efforts against significant human pathogens.

EXAMPLES

General Experimental Procedures.

Optical rotation measurements were obtained on a Perkin-Elmer 241 Polarimeter calibrated using a Rudolph Quartz Control Plate Calibration Standard at sodium D line (at +11.502°). UV spectra were obtained on a UV-visible Molecular Devices SpectraMax M5 spectrophotometer using 1 mL cuvettes with 1.0 cm path lengths at room temperature in solvent MeOH. IR spectra were obtained on a Perkin Elmer Spectrum BX FT-IR spectrometer. Spectrophotometric assays were performed on Molecular Devices SpectraMax M5 384 variable wavelength spectrometer. All NMR spectra were acquired on a Varian INOVA 500 MHz and a Varian INOVA 700 MHz spectrometer at the NMR Facility, Department of Chemistry, University of Michigan. High-resolution APCIMS spectra were measured at the University of Michigan core facility in the Department of Chemistry using an Agilent 6520 Q-TOF mass spectrometer equipped with an Agilent 1290 HPLC system. RP-HPLC was performed using Waters Atlantis® Prep T3 OBD™ 5 µm 19×250 mm column and Luna 5 µm C8(2) 100 Å, AXIA packed column and a solvent system of MeCN and $H_2O$. The LCMS analysis of HPLC fractions was performed on a Shimadzu 2010 EV APCI spectrometer.

Biological Material.

*Streptomyces tempisquensis* (Strain #34946-N9) was isolated from marine sediments collected at Playa Grande mangrove, Costa Rica. The procedure for the isolation of actinomycetes from these samples was previously described by Magarvey et al. [1]. Maintenance and propagation of cultures were performed using standard media and protocols where 500 mg of wet sediment was diluted in 10 mL of sterile water and vortexed for 10 min. Then, 1 mL of this suspension was applied directly to the top of the discontinuous sucrose gradient and centrifuged for 30 minutes at 300×g. 500 µL of the 20%, 30%, and 40% layers were then plated to HVA agar supplemented with 10 µg/mL chlortetracycline, 25 µg/ml cyclohexamide, and 25 µg/ml nalidixic acid. The plates were then incubated at 28° C. for one month. The colony was picked off the plate and streaked onto ISP2 agar until pure. Seed cultures were grown in 17 mL dual position cap tubes containing 2 mL of ISP2 and grown for 4 days on a rotary shaker at 200 rpm. The seed culture was then poured into a 250 mL baffled flask containing 100 mL of ISP2 and grown for 18 days on a rotary shaker at 200 rpm. The culture was centrifuged at 4000 rpm for 10 min to remove the cells and 2 g of XAD16 resin (Sigma-Aldrich, St. Louis, Mo.) contained within a polypropylene mesh bag was added to the broth and incubated overnight on the rotary shaker. The resin bag was removed and placed into 10 ml of MeOH followed by 10 ml of acetone and 10 ml of ethyl acetate. Each of the three fractions was dried in vacuo and reconstituted to a final concentration of 15 mg/mL in DMSO.

Culture Maintenance and Fermentation.

Seed cultures of 100 mL (×5) of ISP2 media (1% malt extract, 0.4% yeast extract, 0.4% dextrose, 3% NaCl) were inoculated with a loopful of vegetative cells from an oatmeal plate (6% oat meal, 1.25% agar, 3% NaCl) culture of *Streptomyces tempisquensis* and incubated with shaking (200 rpm) at 28° C. for 5 days. A 25 mL portion of the seed cultures were transferred into a 2.8 L Fernbach flask containing 1.5 L of the ISP2 medium, and the 39 L fermentation was carried out on a rotary shaker (200 rpm) at 28° C. for 18 days. After 14-18 days of growth, the cultures were harvested by centrifugation. The resulting cell free broth was subjected to solid phase extraction using 15 g of Amberlite XAD-16. The resin was then separated by filtration and subjected to organic extraction using MeOH:EtOAc (1:1).

Isolation and Purification of Baulamycins A-B (6-7). The organic extracts concentrated under vacuum to afford the crude extracts (~10 g) obtained from 39 L culture. The crude extracts were dissolved in 100 mL of H2O and were subjected to a C18-silica gel column (20×2.6 cm, YMC Gel ODS-A, 12 nm, S-150 µm). The C-18 column was eluted with a stepwise gradient of $H_2O$/ACN(100:0→0:100) to give nine fractions (Fr.1-Fr.8), which were concentrated in vacuo to yield fractionated organic materials, respectively. All eight fractions were assayed in the developed in vitro enzymatic assay at 10 and 1.0 ppm. The bio-active Fr.5 was further purified by RP-HPLC on a gradient of 50-90% ACN and was followed by UV/vis photodiode array detection at 210 nm to yield semi-pure compounds 6 (10.3 mg) and 11 (6.4 mg). Compounds were again subjected to re-purification over RP-HPLC on isocratic condition of 59% ACN using C-8 column to get compounds 6 (3.6 mg) and 7 (2.1 mg).

Baulamycin A (6):

Isolated as light yellow amorphous solid: [a] 20$_D$-10.3 (c 0.20, MeOH); IR(film) 3324, 3012, 2952, 2867, 1699, 1602, 1456, 1377, 1143 $cm^{-1}$; UVmax ($\lambda$212 (log e 3.24), 227 (log e 2.93), and 280 (log e 2.51).

Baulamycin B (7):

Isolated as light yellow amorphous solid: [a]20$_D$-10.1 (c 0.20, MeOH); IR(film) 3321, 3016, 2941, 2873, 1702, 1602, 1456, 1365, 1141 $cm^{-1}$; UVmax ($\lambda$) 212 (log e 3.24), 227 (log e 2.93), and 280 (log e 2.51).

Gene Cloning, Expression, and Purification of Enzymes

The sbnE gene was PCR amplified from the genomic DNA of *S. aureus* (Newman). The resulting PCR fragment was cloned into the ligation independent cloning (LIC) vector pMCSG7, containing an N-terminal His6 tag.[2] Cloning of the construct containing the asbA gene into the C-terminal His6 LIC vector pMCSG26 has been described previously.[3] However, a mutation (L299P) was later discovered within the cloned asbA gene sequence. The gene was transferred into pET28a and site directed mutatgenesis was used to revert the sequence to wild type. This reverted construct was utilized in dose response and kinetic studies. The cloning of the asbB gene into the vector pET28b has been previously described.[4] To obtain purified protein from constructs, recombinant *E. coli* BL21 (DE3)-Gold (Stratagene) cells containing the pRARE plasmid (Novagen) encoding tRNAs of rare codons were grown in terrific broth to an A600 nm of ~0.8 at 37° C. and then cooled to 18° C. for an overnight induction with 0.2 mM isopropyl β-D-1-thiogalactopyranoside. Harvested cell pellets were lysed by sonication in a buffer containing 40 mM imidazole, 20 mM HEPES, 300 mM NaCl, 1 mM tris (2-carboxylethyl) phosphine (TCEP), 10% glycerol, a cocktail of protease inhibitors (EDTA-free Complete, Roche), and ~5 mg of lysing enzymes from *Trichoderma harzianum* (Sigma L1412). The cell-free extract was collected by ultracentrifugation at 45,000×g for 45 minutes. The supernatant was subjected to Ni2+ affinity chromatography using a HiTrap™ Chelating HP column (GE healthcare) on a Fast-performance Liquid Chromatography system (FPLC system, Amersham Biosciences) with a linear gradient of 40-300 mM imidazole in 20 mM HEPES, 300 mM NaCl, 1 mM TCEP, and 10% glycerol. Purified protein was dialyzed against 2 L of storage buffer containing 40 mM HEPES, 150 mM NaCl, 1 mM TCEP, and 10% glycerol at pH 8. Protein was concentrated using Amicon Ultra centrifugal molecular weight cutoff filters (Millipore), flash frozen in liquid $N_2$, and stored at −80° C. until analysis.

Natural Product Extract Library.

At the time of screening, the natural product extract (NPE) library at the University of Michigan Center for Chemical Genomics contained ~20,000 extracts. Each extract in the library is derived from marine samples collected from all over the world. Some of these samples are from isolated microbes (n=19055) while others were derived from field-collected biomass samples ("macrosamples," n=800). Previous work describes in detail how these extracts are prepared for the library.[5]

Assay Development and High-Throughput Screening

Fitness of assays for high throughput screening was determined using a Z factor statistical parameter,[6] where p and n represent a positive control and negative control containing no enzyme and no inhibiting compound/extract, respectively:

$$Z = 1 - \frac{3(\sigma_p - \sigma_n)}{|\mu_p - \mu_n|}$$

The NIS hydroxymate-formation assays were conducted as previously described.[7] The NIS-tailored malachite green assays were modified from previously described protocols.[8] Assays were performed in a 384-well plate format with a final volume of 40 μL. Enzymatic activity of both enzymes was found to be most uniform across clear polystyrene microplates produced by Greiner Bio-One (781185). For both assays, conditions were employed that enabled the use of low enzyme concentrations to facilitate optimal detection of any extracts containing low abundance biologically active compounds. For the SbnE reactions, standard final conditions were 25 mM HEPES, pH 7.5, 5 mM $MgCl_2$, 100 μM ATP, 100 μM citrate, 100 μM L-DAP, 0.4 U/mL IPP, and 25 nM SbnE. For AsbA reactions, standard final conditions were 20 mM HEPES, pH 7.5, 1 mM $MgCl_2$, 150 μM ATP, 80 μM citrate, 800 μM spermidine, 0.2667 U/mL IPP, and 100 nM AsbA. Reaction mixtures were split into two solutions: a substrate solution and an enzyme solution to initiate reactions. First, 30 μL of a substrate mix containing HEPES, $MgCl_2$, ATP, citrate, the corresponding polyamine, and IPP was dispensed into 384-well plates using a Multidrop (Thermo Fisher Scientific). Compounds, natural product extracts, or DMSO vehicle controls were then added to wells using a high density replication tool on a Biomek FX liquid handler (Beckman Coulter). To initiate the reactions, 10 μL of an enzyme solution containing HEPES, $MgCl_2$, and purified SbnE or AsbA enzyme was added to the reactions using a Multidrop. For positive controls, an equal volume of a solution only possessing HEPES and $MgCl_2$ was added. Following incubation at room temperature (SbnE: 30 minutes; AsbA: 1 hour), 10 μL of quenching solution of 10 parts malachite green, 2.5 parts 7.5% $(NH_4)_2MoO_4$, and 0.2 parts 11% TWEEN-20 was added to reactions with the Multidrop. Reactions were measured at A600 nm using the Pherastar multimode plate reader (BMG Labtech) after incubating 15 minutes at room temperature.

Dose-Response Assays Against Purified Enzymes

A Mosquito X1 instrument (TTP Labtech) was utilized to dispense varying volumes of 50 mM isolated baulamycin compounds in DMSO onto clean 384 well microplates to make a final range of concentrations between 0 to 550 μM for SbnE and 0 to 1000 μM for AsbA and AsbB after a 40 μL reaction. Spotted plates were stored at −20° C. until analysis. Assays for SbnE and AsbA were carried out at the standard conditions used in screening, as described above. For AsbB reactions, final conditions were 20 mM HEPES, pH 7.5, 1 mM $MgCl_2$, 150 μM ATP, 80 μM citrate, 800 μM N1-(3,4-DHB)-N8-cityl-spermidine (6), 0.2667 U/mL IPP, and 100 nM AsbB. Purification of 6 from *B. anthracis* Sterne 34F2 ΔasbB culture supernatants was performed as described previously.[4] After incubation at room temperature (SbnE: 30 minutes; AsbA/AsbB: 1 hour), reactions were quenched and incubated for 15 minutes as before. Plates were read at A600 with a SpectraMax M5 microplate reader (Molecular Devices). To conserve baulamycin compound, reactions were conducted in duplicate. Percent inhibition was calculated from raw absorbance data using a previously described formula[8c]

$$\% \text{ Inhibition} = 100 \left( \frac{Abs_{sample} - Abs_{\mu_n}}{Abs_{\mu_p} - Abs_{\mu_n}} \right)$$

where p and n represent positive and negative controls respectively.

Resulting data were fitted to the following standard log (inhibitor) versus normalized response model using GraphPad Prism version 5.0 (GraphPad Software). This model demonstrated adequate fit, with $R^2$ values for all SbnE and AsbA curves greater than 0.9.

$$y = \frac{100}{(1 + 10^{(logIC_{50} - X)HillSlope})}$$

Enzyme Kinetic Assays

Reactions were a modification of previously described protocols.[4, 9] Experiments were conducted by varying a single substrate and holding remaining reaction components at a constant saturating level in the presence and absence of inhibitor. The MesG continuous pyrophosphate detection assay was carried out in 384-well microplates (Greiner Bio-One) at 40 μL final volumes in triplicate. For both SbnE and AsbA reactions, constant standard conditions were 50 mM Tris, pH 8, 15 mM $MgCl_2$, 0.5 mM reducing agent (dithiothreitol for SbnE and TCEP for AsbA), 0.001 units/μL PNP, 0.0004 units/μL IPP, 0.4 mM freshly prepared MesG, and 1 μM purified SbnE or AsbA enzyme. SbnE kinetic reactions were conducted at fixed saturating concentrations of L-DAP (40 mM), citrate (10 mM), or ATP (12 mM) while AsbA kinetic reactions were conducted at fixed saturating concentrations of spermidine (40 mM), citrate (20 mM), or ATP (12 mM). The SbnE kinetic reactions with varied concentrations of citrate, L-DAP, or ATP were incubated for 8, 5, or 3 hours, respectively, before the addition of enzyme.

All AsbA reactions were incubated for 10 minutes before initiation of the reaction with enzyme. For both sets of reactions, assays were tested at fixed concentrations of BmcA (0, 10, or 276.4 μM in DMSO) spotted with a Mosquito X1 instrument at varied concentrations of one substrate. Measurements at A360 nm were taken every 30 s over the course of 20 minutes using a SpectraMax plate reader (Molecular Devices). The initial velocities under each set of reaction conditions were subsequently calculated using the slope function in Microsoft Excel. Double-reciprocal (Lineweaver-Bruk) plots of resulting kinetic data were then used to determine the mechanism of inhibition against each substrate. The $K_i$ values were determined from a replot of the slopes from the double-reciprocal plots versus concentration of BmcA.[10]

Dose-Response Assays Against Microbial Cell Cultures.

Strains were grown in LB-Miller medium for iron-rich conditions and LB-Miller medium supplemented with the iron chelator 2,2'-bipyridyl (750 µM for *S. aureus* (Newman) and MRSA (USA 300) strains; 200 µM for the *B. anthracis* 34F2 strain) for iron-depleted conditions. Pelleted cells from cultures grown to mid log phase ($0.4<OD_{600}<0.6$) in iron-rich conditions were washed 3× with medium supplemented with 2,2'-bipyridyl to remove excess iron. Cells re-suspended in iron-depleted media were then used to inoculate fresh 96-well plate cultures at an $OD_{600}$ of 0.003 in either iron-rich or iron-limited conditions. Pure baulamycins at concentrations designated in figures or vehicle controls containing an equal volume of DMSO were added to wells before incubation at 37° C., 200 rpm. For dose response analysis, optical densities after 8 hours of inhibitor-treated (ODI) or DMSO-treated (ODC) cultures were fit to the following previously described [11] sigmoidal equation using GraphPad Prism software:

$$\frac{OD_I}{OD_c} = b + \frac{(a-b)}{1+\left(\frac{[I]}{IC_{50}}\right)^s}$$

16S rDNA PCR Amplification, Cloning, and Sequencing. The genomic DNA of *Streptomyces tempisquensis* was extracted from 1 mL of culture using the Wizard® Genomic DNA Purification Kit (Promega A1120) per the manufacturer's protocol. The 16S rDNA was amplified from the isolated genomic DNA by PCR using the universal primers FC27 (52-AGAGTTTGATCCTGGCTCAG-32) (SEQ ID NO: 1) and RC1492 (52-TACGGCTACCTTGTTAC-GACTT-32) (SEQ ID NO: 2).[12] The PCR reaction mixtures were prepared according to the standard protocol described by GoTaq® Green Master Mix (Promega M7122). A Bio-Rad iCycler thermocycler was used for template amplification with the following PCR cycle conditions: an initial denaturation step at 98° C. for 30 s, followed by 30 cycles of 95° C. for 30 s, 50° C. for 30 s, 72° C. for 90 s, and a final extension of 72° C. for 7 min. The PCR products were purified using the Wizard® SV Gel DNA Recovery Kit (Promega A9282). The purified PCR fragments were modified to add a 3' A overhang using Taq DNA polymerase. Ligation of the modified product into pGEM®-T Easy vector (Promega) was completed with T4 DNA Ligase (NEB M0202) according to the manufacturer's standard protocol. The resulting pGEM-16S rDNA construct was transformed into chemically competent *E. coli* DH-5a cells. The transformation reactions were mixed with 40 µL of X-gal (20 mg/mL in DMSO) and 40 µL IPTG (100 mM in sterile $H_2O$) before plating on LB agar plates containing ampicillin (250 µg/mL). Plates were incubated overnight at 37° C. for a-complementation. After incubation, single white colonies were used to inoculate LB media in sterile culture tubes (×6). All the tubes were incubated at 37° C., 250 rpm for overnight growth.

Plasmid DNA was isolated from pelleted cells using the Wizard® SV Miniprep Kit (Promega A1460) and sequenced using T7 and SP6 primers. The 16S sequence for *S. tempisquensis* has been given the GenBank accession number KF954543.

Phylogenetic Analysis

Phylogenetic analyses were conducted in GENEIOUS R6. Geneious version 1.8 created by Biomatters. Available from http://www.geneious.com/. The evolutionary history was inferred using the Neighbor-Joining method. The bootstrap consensus tree inferred from 1000 replicates was taken to represent the evolutionary history of the taxa analyzed.

REFERENCES (1) Andersson, et al. FEMS Microbiol. Rev. 2011, 35, 901.
(2) Fischbach, et al. Science 2009, 325, 1089.
(3) Nathan, Sci Transl Med. 2012, 4.
(4) Livermore, J. Antimicrob. Chemother. 2011, 66, 1941.
(5) Moir, et al. Curr. Opin. Pharmacol. 2012, 12, 535.
(6) Quadri, Infect. Disord. Drug Targets 2007, 7, 230.
(7) Miethke, et al. Microbiol. Mol. Biol. Rev. 2007, 71, 413.
(8) Gupte, et al. J. Med. Chem. 2008, 51, 7495.
(9) Ferreras, et al. Nat. Chem. Biol. 2005, 1, 29.
(10) Neres, et al. J. Med. Chem. 2008, 51, 5349.
(11) Somu, et al. J. Med. Chem. 2006, 49, 31.
(12) Klevens, et al. JAMA 2007, 298, 1763.
(13) Sweeney, et al. Am. J. Respir. Crit. Care Med. 2011, 184, 1333.
(14) See: http://www.cdc.gov/drugresistance/diseasesconnectedar.html
(15) Haley, et al. Microbes Infect. 2012, 14, 217.
(16) Hotta, et al. Microbiology (Reading, U. K.) 2010, 156, 1918.
(17) Haag, et al. FEMS Microbiol. Lett. 1994, 115, 125.
(18) Drechsel, et al. Biometals 1993, 6, 185.
(19) Dale, et al. Infect. Immun. 2004, 72, 29.
(20) Cheung, et al. Mol. Microbiol. 2009, 74, 594.
(21) Cheung, et al. Chem. Biol. 2012, 19, 1568.
(22) Beasley, et al. BMC Microbiol. 2011, 11, 199.
(23) Cendrowski, et al. Mol. Microbiol. 2004, 51, 407.
(24) Koppisch, et al. Biometals 2005, 18, 577.
(25) Lee, et al. J. Bacteriol. 2007, 189, 1698.
(26) Pfleger, et al. Biochemistry 2007, 46, 4147.
(27) Pfleger, et al. Proc. Natl. Acad. Sci. U.S.A. 2008, 105, 17133.
(28) Oves-Costales, et al. J. Am. Chem. Soc. 2007, 129, 8416.
(29) Fox, et al. Biochemistry 2008, 47, 12251.
(30) Nusca, et al. J. Biol. Chem. 2012, 287, 16058.
(31) Oves-Costales, et al. Chem. Commun. (Cambridge, U. K.) 2009, 43, 6530.
(32) Challis, Chembiochem 2005, 6, 601.
(33) Newman, et al. J. Nat. Prod. 2007, 70, 461.
(34) Newman, et al. J. Nat. Prod. 2012, 75, 311.
(35) Montaser, et al. Future Med Chem 2012, 3, 1475.
(36) Itaya, et al. Clin. Chim. Acta 1966, 14, 361.
(37) Pegan, et al. Comb. Chem. High Throughput Screening 2010, 13, 27.
(38) McQuade, et al. Anal. Biochem. 2009, 386, 244.
(39) Matsumori, et al. J. Org. Chem. 1999, 64, 866.
(40) Morinaka, et al. Org. Lett. 2011, 13, 6338.
(41) Huang, et al. Org. Lett. 2012, 14, 1254.
(42) Peng, et al. J. Am. Chem. Soc. 2010, 132, 3277.
(43) Webb, Proc. Natl. Acad. Sci. U.S.A. 1992, 89, 4884.
(44) Wilson, et al. Anal. Biochem. 2010, 404, 56.
(45) Brandish, et al. Antimicrob. Agents Chemother. 1996.
(46) Schmelz, et al. J. Mol. Biol. 2011, 412, 495.
(47) Roemer, et al. Chem. Biol. 2011, 18, 148.

(48) Gibson, et al. Biochim. Biophys. Acta 1969, 192, 175.
(49) Warner, et al. Infect. Immun. 1981, 33, 540.
(50) de Lorenzo, et al. J. Bacteriol. 1986, 167, 350.
(51) de Lorenzo, et al; Neilands, J. B. 1986, 165, 570.

EXAMPLE CITATIONS

[1] Magarvey, et al, *Appl. Environ. Microbiol.* 2004, 70, 7520-7529.
[2] Stols, et al., *Protein Expr. Purif.* 2002, 8-15.
[3] Eschenfeldt, et al, *J. Struct. Funct. Genomics* 2010, 11, 31-39.
[4] Nusca, et al, *J. Biol. Chem.* 2012, 287, 16058-16072.
[5] Cruz, et al, *Chem. Biol.* (Oxford, U. K) 2011, 18, 1442-1452.
[6] Zhang, *J. Biomol. Screening* 1999, 4, 67-73.
[7] Kadi, et al, *Methods Enzymol.* 2009, 458, 431-457.
[8] (a) Itaya, et al, *Clin. Chim. Acta* 1966, 14, 361-366; (b) McQuade, et al, *Anal. Biochem.* 2009, 386, 244-250; (c) Pegan, et al, *Comb. Chem. High Throughput Screen.* 2010, 38.
[9] (a) Wilson, et al, *Anal. Biochem.* 2010, 404, 56-63; (b) Upson, et al, *Anal. Biochem.* 1996, 243, 41-45; (c) Webb, *Proc. Natl. Sci. U.S.A.* 1992, 89, 4884-4887.
[10] (a) Campbell, et al, *Biochemistry*, Cengage Learning, 2011; (b) Kong, et al, *J. Ethnopharmacol.* 2004, 91, 351-355.
[11] Ferreras, et al, *Nat. Chem. Biol.* 2005, 1, 29.
[12] Rainey, et al, *Int. J. Syst. Bacteriol.* 1996, 46, 1088-1092.

prising a pharmaceutically acceptable excipient and a compound of formula (I), or a pharmaceutically acceptable salt thereof,

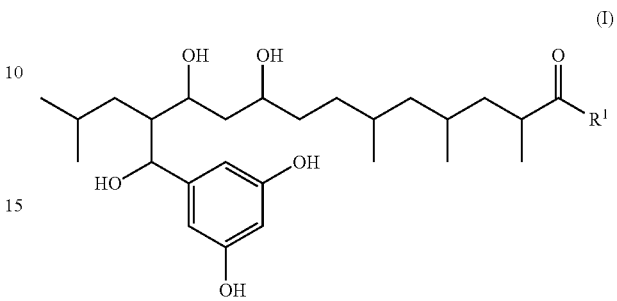

wherein $R^1$ is a $C_{1-6}$alkyl;

said composition contacted in an amount sufficient to inhibit the NIS synthetase.

2. The method of claim 1, wherein the NIS synthetase is a Type A NIS synthetase.

3. The method of claim 1, wherein the NIS synthetase is AsbA or SbnE.

What is claimed:

1. A method of inhibiting a nonribosomal peptide synthetase independent siderophore (NIS) synthetase comprising contacting the NIS synthetase with a composition com- 4. The method of claim 1, wherein the compound of formula (I), or pharmaceutically acceptable salt thereof, has a stereochemistry as shown in formula (IA):

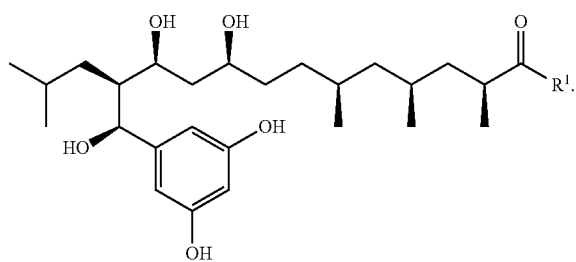 [SMILES: CCC(=O)[C@@H](C)C[C@@H](C)C[C@@H](C)CC[C@H](O)C[C@H](O)[C@H](CC(C)C)[C@H](O)c1cc(O)cc(O)c1]
(IA)
5. The method of claim 1, wherein the compound of formula (I) has a structure
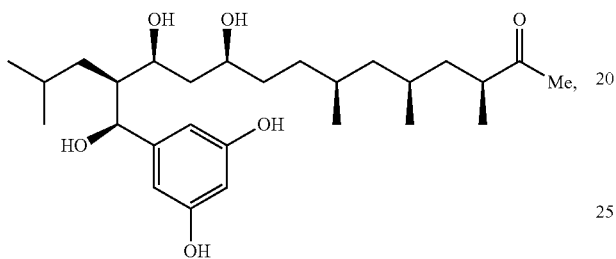
or a pharmaceutically acceptable salt thereof.
6. The method of claim 1, wherein the compound of formula (I) has a structure
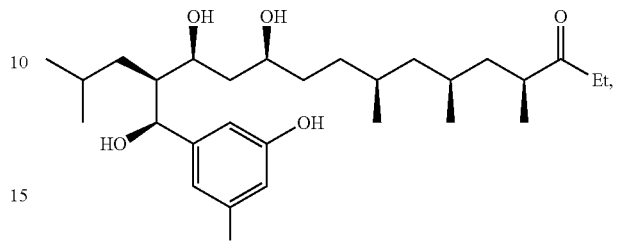
or a pharmaceutically acceptable salt thereof.
* * * * *

SEQUENCE LISTING

```
<160> NUMBER OF SEQ ID NOS: 2

<210> SEQ ID NO 1
<211> LENGTH: 20
<212> TYPE: DNA
<213> ORGANISM: Streptomyces tempisquensis

<400> SEQUENCE: 1
agagtttgat cctggctcag                                       20

<210> SEQ ID NO 2
<211> LENGTH: 22
<212> TYPE: DNA
<213> ORGANISM: Streptomyces tempisquensis

<400> SEQUENCE: 2
tacggctacc ttgttacgac tt                                    22
```